United States Patent

Chesney et al.

[11] Patent Number: 6,159,166
[45] Date of Patent: *Dec. 12, 2000

[54] SENSOR AND METHOD FOR SENSING ARTERIAL PULSE PRESSURE

[75] Inventors: Charles F. Chesney, Sunfish Lake; Dennis J. Morgan, Crystal, both of Minn.; Eugene A. O'Rourke, Lackawanna, N.Y.; Michael T. Riggs, Batavia, N.Y.; Fred Randall Thornton, Lancaster, N.Y.

[73] Assignee: Hypertension Diagnostics, Inc., Eagan, Minn.

[*] Notice: This patent issued on a continued prosecution application filed under 37 CFR 1.53(d), and is subject to the twenty year patent term provisions of 35 U.S.C. 154(a)(2).

[21] Appl. No.: 09/045,018

[22] Filed: Mar. 20, 1998

[51] Int. Cl.⁷ ........................................................ A61B 5/02

[52] U.S. Cl. ........................ 600/586; 600/502; 600/503; 600/500; 381/173; 381/176; 73/727

[58] Field of Search .................................... 600/502, 500, 600/503, 514, 528, 586; 381/173, 176; 73/645, 632, 703, 721, 715, 727

[56] References Cited

U.S. PATENT DOCUMENTS

| | | | |
|---|---|---|---|
| 3,651,353 | 3/1972 | Hugli et al. | 381/173 |
| 4,409,983 | 10/1983 | Albert | 128/690 |
| 4,431,873 | 2/1984 | Dunn et al. | 381/173 |

(List continued on next page.)

FOREIGN PATENT DOCUMENTS

| | | | |
|---|---|---|---|
| 0357275A1 | 3/1990 | European Pat. Off. | A61B 5/11 |
| 4190521 | 3/1990 | Germany | H04R 1/46 |
| 87/02233 | 4/1987 | WIPO | A61B 7/04 |
| 92/09232 | 6/1992 | WIPO | A61B 5/0255 |
| 94/05207 | 3/1994 | WIPO | A61B 7/04 |
| 95/06525 | 3/1995 | WIPO | B06B 1/06 |

OTHER PUBLICATIONS

"Acoustic Contact Sensor", *Apollo Research Corp.*, Model 701010, 4, 5 Pages.

"Aging Arteries", *Harvard Heart Letter*, 8(2), 4 pgs., (Oct. 1997).

"Guide to Modern Piezoelectric Ceramics", Advertising Material from Morgan Matroc, Inc. (undated), 6 pages.

"Harvard Heart Letter", *Harvard Medical School*, 7(7), 5 pgs., (Mar. 1997).

"Nellcor's N–CAT Continuous Noninvasive Blood Pressure Monitor, Model N–500", Product Publication by Nellcor, Inc., 9 pages, (1991).

(List continued on next page.)

*Primary Examiner*—Cary O'Connor
*Assistant Examiner*—Navin Natnithithadha
*Attorney, Agent, or Firm*—Schwegman, Lundberg, Woessner & Kluth, P.A.

[57] ABSTRACT

A method and a pulse pressure sensor for sensing an arterial pulse pressure waveform. In one embodiment, the pulse pressure sensor includes a housing, a diaphragm, a piezoelectric device, and a self-contained amplifier. The skin-contact diaphragm is attached across a recess or opening in the housing. The piezoelectric device has a first portion mounted in a fixed relationship to the housing and a second portion displacementally coupled to the diaphragm. The solid-state amplifier has a signal input coupled to the piezoelectric device, wherein the piezoelectric device and amplifier together have a frequency response at least including a range from below approximately 0.1 hertz to above approximately 250 hertz. In one such embodiment, the housing and the skin-contact diaphragm of the sensor are stainless steel. In one such embodiment, the diaphragm has a skin-contact surface with a skin-contact dimension of between approximately 0.4 inch and 0.6 inch. In one embodiment, the sensor includes a solid-state amplifier that includes a high-input-impedance MOSFET input stage having an input resistance high enough to provide a frequency response that extends below approximately 0.1 hertz.

20 Claims, 19 Drawing Sheets

U.S. PATENT DOCUMENTS

| | | | |
|---|---|---|---|
| 4,672,976 | 6/1987 | Kroll | 600/528 |
| 4,784,154 | 11/1988 | Shirley et al. | 600/528 |
| 4,889,133 | 12/1989 | Nelson et al. | 128/681 |
| 4,947,859 | 8/1990 | Brewer et al. | 600/528 |
| 4,949,710 | 8/1990 | Dorsett et al. | 128/680 |
| 4,993,422 | 2/1991 | Hon et al. | 128/672 |
| 5,035,247 | 7/1991 | Heinmann | 600/528 |
| 5,211,177 | 5/1993 | Chesney et al. | 128/691 |
| 5,240,007 | 8/1993 | Pytel et al. | 128/672 |
| 5,241,964 | 9/1993 | McQuilkin | 128/672 |
| 5,269,312 | 12/1993 | Kawamura et al. | 128/690 |
| 5,316,004 | 5/1994 | Chesney et al. | 128/672 |
| 5,337,750 | 8/1994 | Walloch | 128/680 |
| 5,524,637 | 6/1996 | Erickson | 128/779 |
| 5,544,651 | 8/1996 | Wilk | 128/633 |
| 5,551,437 | 9/1996 | Lotscher | 128/672 |
| 5,551,438 | 9/1996 | Moses | 128/672 |
| 5,560,366 | 10/1996 | Barada et al. | 128/681 |
| 5,577,508 | 11/1996 | Medero | 128/681 |
| 5,584,298 | 12/1996 | Kabal | 128/672 |
| 5,590,661 | 1/1997 | Ohmori et al. | 128/672 |
| 5,592,401 | 1/1997 | Kramer | 364/550 |
| 5,617,868 | 4/1997 | Harada et al. | 128/672 |
| 5,623,933 | 4/1997 | Amano et al. | 128/687 |
| 5,638,823 | 6/1997 | Akay et al. | 128/691 |
| 5,640,964 | 6/1997 | Archibald et al. | 128/672 |
| 5,642,733 | 7/1997 | Archibald et al. | 128/672 |
| 5,647,369 | 7/1997 | Petrucelli et al. | 128/672 |
| 5,649,542 | 7/1997 | Archibald et al. | 128/681 |
| 5,671,750 | 9/1997 | Shinoda | 128/672 |
| 5,704,362 | 1/1998 | Hersh et al. | 128/280 |
| 5,752,919 | 5/1998 | Schrimpf | 600/493 |

OTHER PUBLICATIONS

"Non–Invasive Arterial Waveform Analysis and Blood Pressure Measurement", Pulse Dynamic Oscillometrics Clinical Information, Pulse Metric, Inc., San Diego, CA, 4.

"Non–Invasive Blood Pressure/Pulse Rate Monitoring and Recording System", Portfolio™ Health Series, 6 pages.

Bing, et al., "Reversal of Acetylcholine Effect on Atherosclerotic Coronary Arteries by Estrogen: Pharmacologic Phenomenon of Clinical Importance?", *Journal of the American college of Cardiology*, 3 pages, (Aug. 1992).

Brinton, et al., "Arterial Compliance by Cuff Sphygmomanometer", *Hypertension, 28(4)*, Application to Hypertension and Early Changes in Subjects at Genetic Risk, 599–603, (Oct. 1996).

Brinton, et al., "The Development and Validation of a New Non–invasive Method to Evaluate Ventricle Function During Routine Blood Pressure Monitoring", *American Journal of Hypertension, 10(4) Part 2 (Abstract Issue)*, 2 pages, (1997).

Cohn, J.N., et al., "Noninvasive Pulse wave Analysis for the early detection of Vascular Disease", *Hypertension, 26*, 503–508, (Sep., 1995).

Glasser, et al., "Vascular Compliance and Cardiovascular Disease", *AJH, 10(10), Part 1*, 1175–1189, (Oct. 1997).

Kluger, J., "Beyond Cholesterol", *Time*, 48, (Aug. 4, 1997).

McVeigh, et al., "Vascular Abnormalities Associated with Long–term Cigarette Smoking Identified by Arterial Waveform Analysis", *The American Journal of Medicine, 102*, 227–231, (Mar. 1997).

Rajkumar, et al., "Hormonal Therapy Increases Arterial Compliance in Postmenopausal Women", *JACC, 30(2)*, 350–356, (Aug. 1997).

Simon, et al., "Detection of Preclinical Atherosclerosis May Optimize the Management of Hypertension", *AJH, 10(7) Part 1*, 813–824, (Jul. 1997).

Yoshizawa, et al., "Classical but Effective Techniques for Estimating Cardiovascular Dynamics", *IEEE Engineering in Medicine & Biology Magazine, 16(5)*, 106–112, (Sep.–Oct. 1997).

SENSOR AND METHOD FOR SENSING ARTERIAL PULSE PRESSURE

CROSS REFERENCES TO RELATED INVENTIONS

This invention is related to co-pending application entitled "APPARATUS AND METHOD FOR HOLDING AND POSITIONING AN ARTERIAL PULSE PRESSURE SENSOR" and to co-pending application entitled "APPARATUS AND METHOD FOR BLOOD PRESSURE PULSE WAVEFORM CONTOUR ANALYSIS" both filed on even date herewith and incorporated herein by reference.

FIELD OF THE INVENTION

This invention relates to the field of medical sensors, and, more specifically, to a method and apparatus of sensing an arterial pulse pressure, and, in particular, the blood pressure waveform in the radial artery of the human body.

BACKGROUND OF THE INVENTION

Conventionally, blood pressure has been measured by one of four basic methods: invasive, oscillometric, auscultatory and tonometric. The invasive method, also known as an arterial-line method (or "A-line"), typically involves insertion of a needle or catheter into an artery. A transducer connected by a fluid column to the needle or catheter is used to determine exact arterial pressure. With proper instrumentation, systolic, diastolic, and mean arterial pressures may be determined, and a blood-pressure waveform may be recorded. This invasive method is difficult to set up, is expensive and time consuming, and involves a potential medical risk to the subject or patient. Set up of the arterial-line method poses technical problems. Resonance often occurs and causes significant errors. Also, if a blood clot forms on the end of the needle or catheter, or the end of the needle or catheter is located against an arterial wall, a large error may result. To eliminate or reduce these errors, the setup must be checked, flushed, and adjusted frequently. A skilled medical practitioner is required to insert a needle or catheter into the artery, which contributes to the expense of this method. Medical complications are also possible, such as infection, nerve and/or blood vessel damage.

The other three traditional methods of measuring blood pressure are non-invasive. The oscillometric method measures the amplitude of blood pressure oscillations in an inflated cuff. Typically, the cuff is placed around the upper arm of the patient and then pressurized to different levels. Mean pressure is determined by sweeping the cuff pressure and determining the cuff pressure at the instant the peak amplitude occurs. Systolic and diastolic pressure is determined by cuff pressure when the pressure oscillation is at some predetermined ratio of peak amplitude.

The auscultatory method also involves inflation of a cuff placed around the upper arm of the patient. After inflation of the cuff to a point where circulation is stopped, the cuff is permitted to deflate. Systolic pressure is indicated when Korotkoff sounds begin to occur as the cuff is deflated. Diastolic pressure is indicated when the Korotkoff sounds become muffled or disappear.

The fourth method used to determine arterial blood pressure has been tonometry. The tonometric method typically involves a transducer positioned over a superficial artery. The transducer may include an array of pressure-sensitive elements. A hold-down force is applied to the transducer in order to partially flatten the wall of the underlying artery without occluding the artery. Each of the pressure-sensitive elements in the array typically has at least one dimension smaller than the lumen of the underlying artery in which blood pressure is measured. The transducer is positioned such that at least one of the individual pressure sensitive elements is over at least a portion of the underlying artery. The output from one or more of the pressure-sensitive elements is selected for monitoring blood pressure. These tonometric systems either use an upper-arm cuff to calibrate blood-pressure values, or they measure a reference pressure directly from the wrist and correlate this with arterial pressure. However, when a patient moves, recalibration of the tonometric system is often required because the system may experience a change in electrical gains. Because the accuracy of such tonometric systems depends upon the accurate positioning of the individual pressure sensitive element over the underlying artery, placement of the transducer is critical. Consequently, placement of the transducer with these tonometric systems is time-consuming and prone to error. Also, expensive electromechanical systems guided by software/hardware computer approaches are often used to assist in maintaining transducer placement.

The oscillometric, auscultatory and tonometric methods measure and detect blood pressure by sensing force or displacement caused by blood pressure pulses within the underlying artery that is compressed or flattened. The blood pressure is sensed by measuring forces exerted by blood pressure pulses in a direction perpendicular to the underlying artery. However, with these methods, the blood pressure pulse also exerts forces parallel to the underlying artery as the blood pressure pulses cross the edges of the sensor which is pressed against the skin overlying the underlying artery of the patient. In particular, with the oscillometric and the auscultatory methods, parallel forces are exerted on the edges or sides of the cuff. With the tonometric method, parallel forces are exerted on the edges of the transducer. These parallel forces exerted upon the sensor by the blood pressure pulses create a pressure gradient across the pressure-sensitive elements. This uneven pressure gradient creates at least two different pressures, one pressure at the edge of the pressure-sensitive element and a second pressure directly beneath the pressure sensitive element. As a result, the oscillometric, auscultatory and tonometric methods can produce inaccurate and inconsistent blood pressure measurements.

Further, the oscillometric and auscultatory methods are directed at determining the systolic, diastolic, and/or mean blood pressure values, but are not suited to providing a calibrated waveform of the arterial pulse pressure.

Until now, there has been no good way to obtain, non-invasively, an accurate, repeatable blood-pressure waveform from the radial artery.

SUMMARY OF THE INVENTION

The present invention provides an arterial pulse pressure sensor and a method for sensing an arterial pulse pressure waveform.

In one embodiment, an arterial pulse pressure sensor 100 includes a housing, a diaphragm, a piezoelectric device, and a self-contained amplifier. The skin-contact diaphragm is attached across a recess or opening in the housing. The piezoelectric device has a first portion mounted in a fixed relationship to the housing and a second portion displacementally coupled to the diaphragm. The solid-state amplifier has a signal input coupled to the piezoelectric device, wherein the piezoelectric device and amplifier together have a frequency response at least including a range from below approximately 1 hertz to above approximately 250 hertz. In another embodiment, the low-end frequency response extends to 0.1 hertz. In one such embodiment, the housing and the skin-contact diaphragm of the sensor are medical-grade stainless steel. In one such embodiment, the diaphragm has a skin-contact surface with a skin-contact dimension of between approximately 0.4 inch and 0.6 inch.

In one embodiment, the sensor includes a solid-state amplifier that includes a MOSFET input stage having an input resistance high enough to provide a frequency response that extends below approximately 0.1 hertz. In one such embodiment, the sensor includes a solid-state amplifier that further includes an input/output signal wire, a ground signal path, a voltage divider, a drain resistor, a gate resistor, a MOSFET input transistor, and a bipolar output transistor. The voltage divider is coupled between the input/output signal wire and the ground. The MOSFET input transistor has a gate coupled to receive a signal from the piezoelectric device, a source coupled to an intermediate point of the voltage divider, and a drain, wherein the drain resistor is coupled between the drain and the ground, and the gate resistor is coupled between the gate and the ground. The bipolar output transistor has a collector coupled to the input/output signal wire, an emitter coupled to the ground, and a base coupled to the drain of the input transistor.

In one embodiment, the sensor has a piezoelectric device that includes a piezoelectric double-plate ceramic element (DPCE), wherein two thin plates are laminated and bonded together so they amplify their piezoelectric actions.

In one embodiment, a constant-current source is connected to the input/output wire.

BRIEF DESCRIPTION OF THE DRAWINGS

FIG. 1O-1 shows a side view of one embodiment of DPCE post 172.

FIG. 1O-2 shows a side view of another embodiment of DPCE post 172.

DESCRIPTION OF PREFERRED EMBODIMENTS

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

Figure 1A:
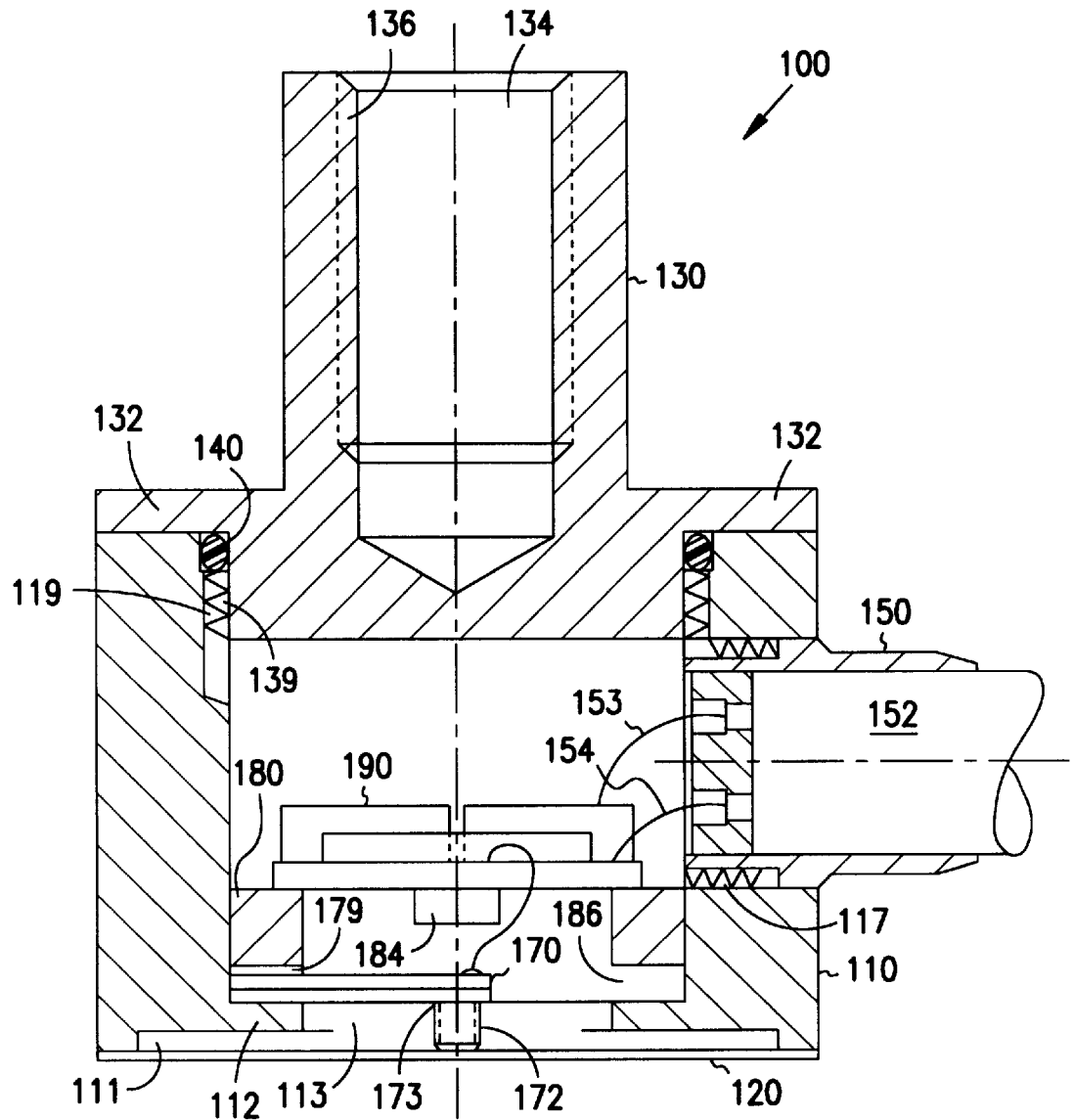
FIG. 1A shows a cross-section view of one embodiment of arterial pulse pressure sensor 100.

FIG. 1A shows a cross-section view of one embodiment of assembled arterial pulse pressure sensor 100. In the embodiment shown, arterial pulse pressure sensor 100 includes housing 110, diaphragm 120 which is welded to housing 110 (in one embodiment, laser welded), cover 130 which is screwed onto housing 110 and sealed using O-ring 140, cable adaptor 150 which is screwed to housing 110 and glued and sealed to signal/power cable 152 with epoxy, piezoelectric double-plate ceramic element (DPCE) 170 which is attached using epoxy between DPCE-holder ring 180 and shelf 112 of housing 110, and amplifier 190 which is mounted to DPCE-holder ring 180. Since one embodiment uses a piezoelectric DPCE 170, this embodiment is described as having a DPCE-holder ring 180 and a DPCE post 172; it is to be understood that other embodiments include single-plate ceramic piezoelectric elements or other types of pressure-sensing elements in place of DPCE 170, and will have a corresponding holder ring and post in some of those embodiments. The adjective term "DPCE" applies to those embodiments having a DPCE 170 sensing element, but not to other embodiments having other types of sensing elements.

In one embodiment, housing 110, diaphragm 120, cover 130, cable adaptor 150, and DPCE-holder ring 180 are medical-grade stainless steel (type 316L), in order to be durable and relatively inert for the intended use of skin-contact arterial pulse-pressure sensing. Deflection of diaphragm 120 causes DPCE 170 to flex and thereby generate an electrical signal, which in turn is amplified and conditioned by amplifier 190 and coupled to signal/power cable 152. Signal/power cable 152 (also called input/output cable 152) provides both delivery of input electrical power to amplifier 190, as well as receiving the output signal from amplifier 190, all using only two signal conductors (e.g., input/output wire 153, and ground 154). In one embodiment, cable 152 is connected to a constant-current source by connector 159 (e.g., a 2 milliamp constant current source), and amplifier 190 then provides a varying voltage (on the same signal wire that provides the constant current) linearly proportional to the pressure on diaphragm 120. An external circuit then receives and processes the arterial pulse-pressure waveform from the varying voltage.

Female threads 119 that are machined into the upper bore of housing 110 mate with male threads 139 of cover 130. O-ring gasket 140 forms a seal between housing 110 and cover 130. (In another embodiment, an O-ring gasket is also provided to seal between housing 110 and cable adaptor 150. In one preferred embodiment though, a potting epoxy is used instead of an O-ring to seal between housing 110 and cable adaptor 150.) Female threads 117 in the sidewall bore of housing 110 mate with male threads 157 of cable adaptor 150. In one embodiment, signal/power cable 152 is secured into the opening in cable adaptor 150 using epoxy, and cured in an oven at 150° F. for a minimum of 30 minutes. In the embodiment shown, DPCE-holder ring 180 has a slot 184 through one wall, and a slot 186 through two walls. One end of DPCE 170 is located mostly within slot 186 (i.e., the bottom surface of DPCE 170 extends slightly below the bottom surface of DPCE-holder ring 180 in order to make electrical and mechanical contact with shelf 112 of housing 110), but is electrically insulated from DPCE-holder ring 186 by a layer of epoxy 179.

Figure 1B:
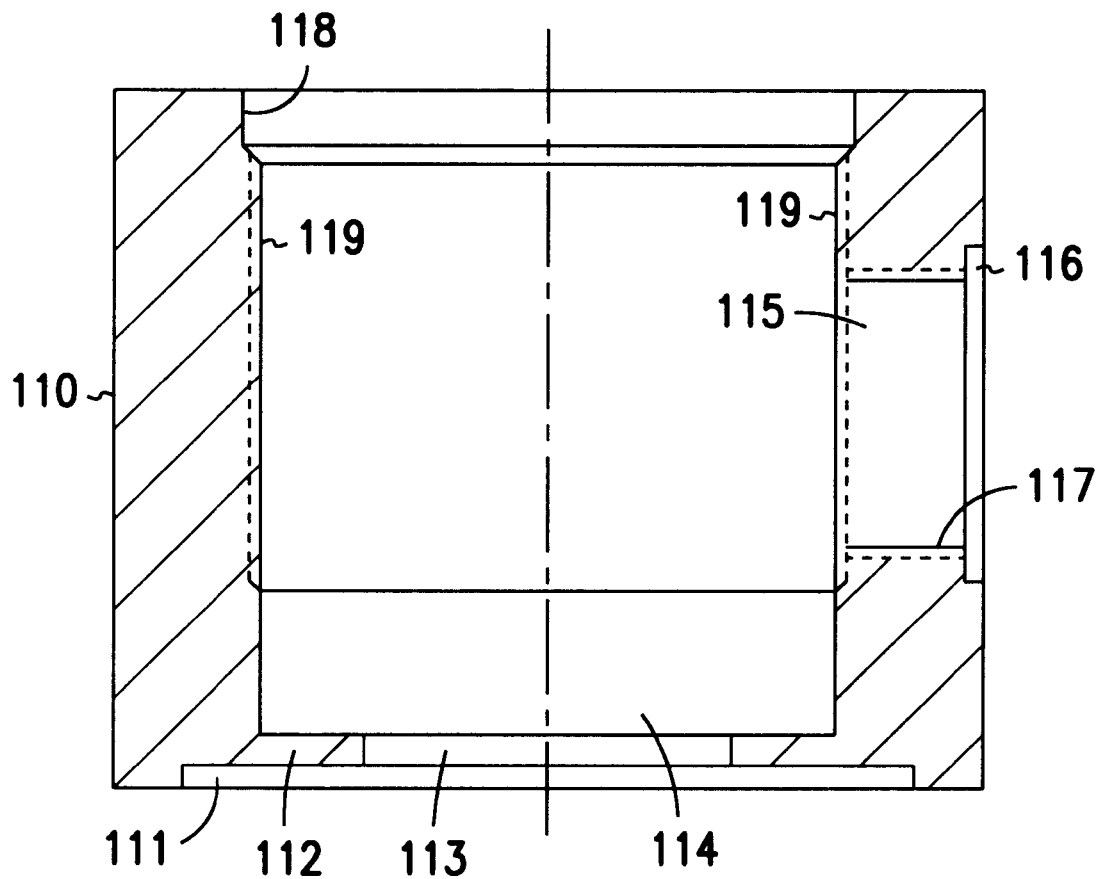
FIG. 1B shows a cross-section view of housing 110.

In one embodiment (shown in cross-section in FIG. 1B), housing 110 is made from a (type 316L) medical-grade stainless-steel cylinder having a 0.5 inch diameter and a 0.4 inch height. A 0.015 inch-deep, 0.44 inch diameter, flat-bottomed, cylindrical lower hole (or "opening") 111 is machined into the bottom surface. A 0.328 diameter, flat-bottomed, cylindrical upper hole 114 is machined into the top surface to a plane 0.039 inch from the bottom surface. A 0.213 diameter cylindrical middle hole 113 connects the upper hole 114 to the lower hole 111, leaving shelf 112. (In another such embodiment, hole 111 is machined 0.039 inch deep, and a washer, 0.024 inch thick and having an approximately 0.44 inch outer diameter and a 0.213 inch hole is welded into hole 111 to form shelf 112—leaving a 0.015 inch lower hole 111, substantially as shown here.) The top of hole 114 is threaded to a depth of 0.20 inches minimum with threads 119 that match threads 139 of cover 130. The top of hole 114 is also counter bored at a diameter of 0.365 inches to a depth of 0.030 inches for O-ring gasket 140. A hole 115 is machined through the side of housing 110, centered at 0.225 inches above the plane of the bottom surface of housing 110, and is threaded with threads 117 that correspond to the male threads 157 of cable adaptor 150. Shoulder 116 is counter bored into the outer edge of hole 115. The outer edges of the top and bottom surfaces, respectively, of housing 110 are left sharp in order to minimize any seam between housing 110, and cover 130 and diaphragm 120, respectively.

Figure 1C:
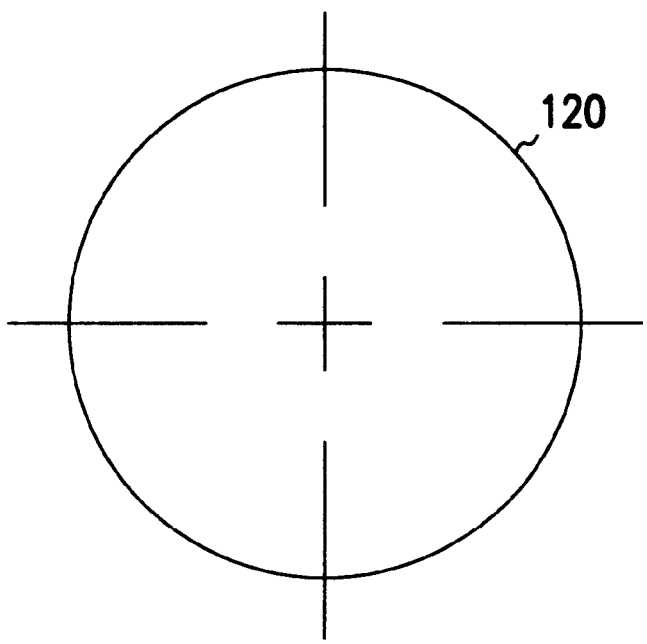
FIG. 1C shows a bottom view (not to scale) of diaphragm 120.
Figure 1D:
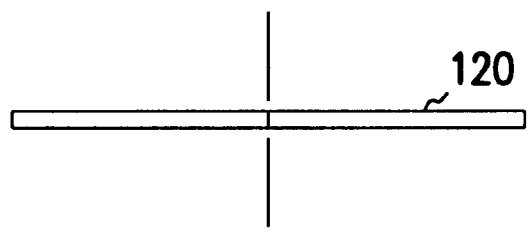
FIG. 1D shows a side view (not to scale) of diaphragm 120.
Figure 1E:
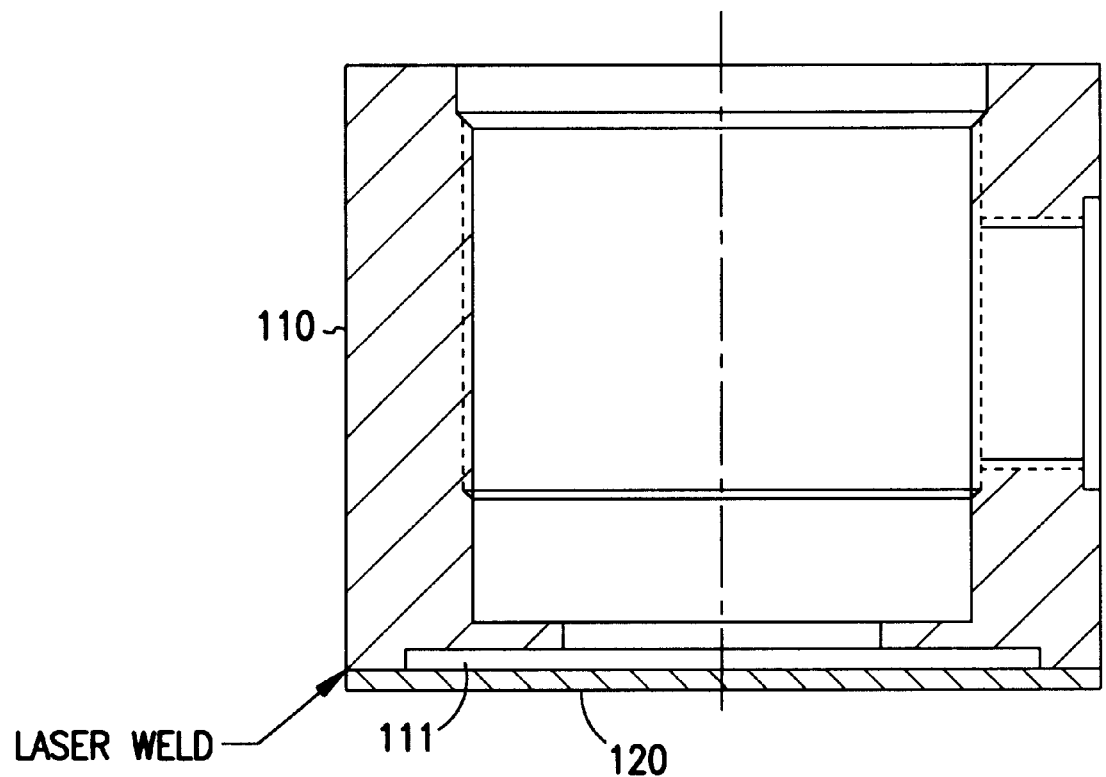
FIG. 1E shows a cross-section view of diaphragm 120 welded in place to the bottom surface of housing 110 across opening 111.

FIG. 1C shows a bottom view, and FIG. 1D shows a side view (not to scale) of one embodiment of diaphragm 120. In this embodiment, diaphragm 120 is a disc of medical-grade stainless steel (type 316L) having a diameter of 0.5 inches and a thickness of 0.006 inches. The thickness of diaphragm 120 is chosen to be thick enough to impart ruggedness and durability to arterial pulse pressure sensor 100, yet thin enough to provide the sensitivity and frequency response desired. In one embodiment, diaphragm 120 is laser-welded to the bottom surface of housing 110 across opening 111, using a pulsed NdYAG laser welder, with weld settings of: pulse rate—40/sec; pulse width—1; joules/pulse—0.3; and seconds/rev—5.5. Other types of welding such as Tungsten Inert Gas (TIG), may be used. A diaphragm welding pilot is used to hold the housing and a diaphragm welding heat sink is also used. The result is as shown in the cross-section view presented as FIG. 1E.

Figure 1F:
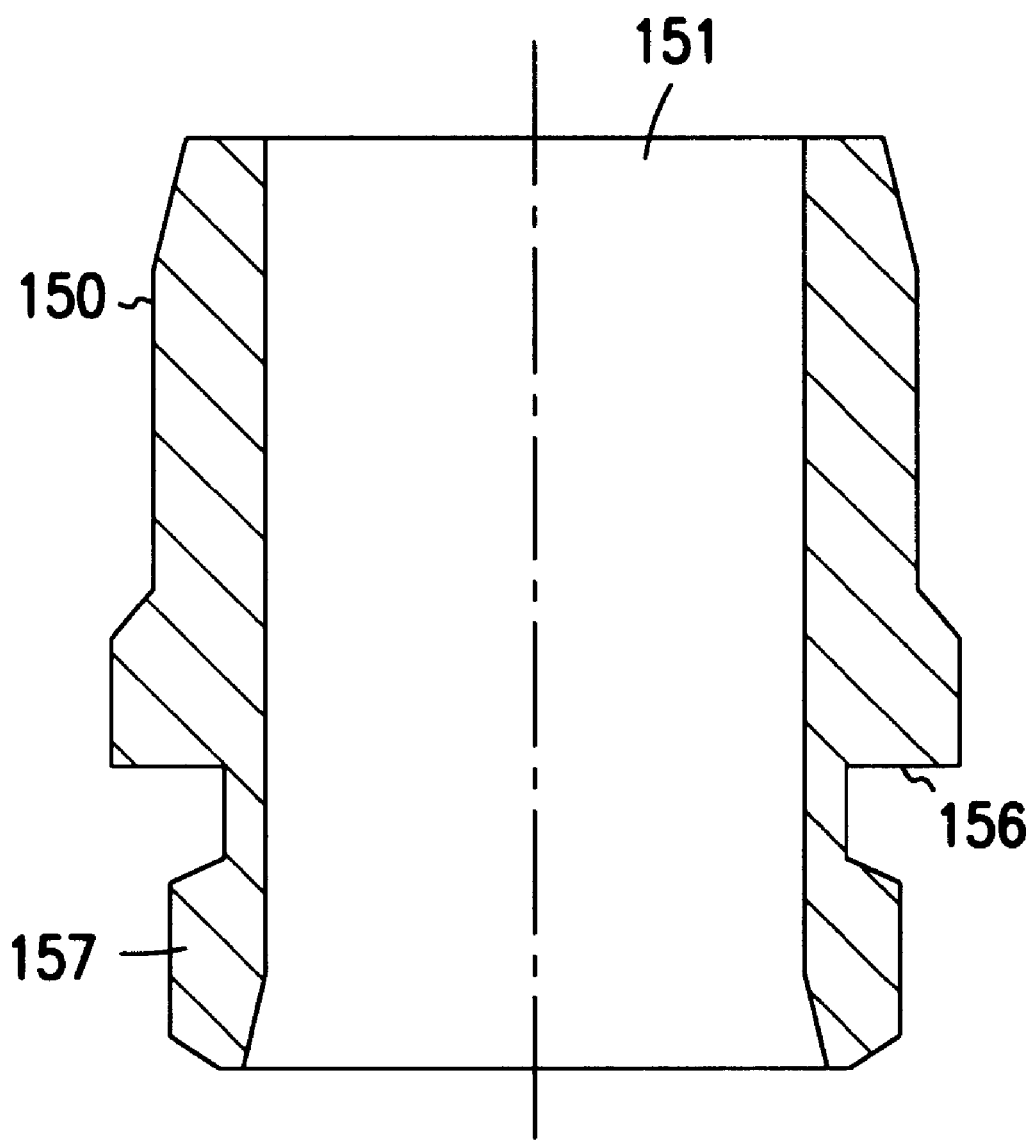
FIG. 1F shows a cross-section view of cable adaptor 150.

FIG. 1F shows a cross-section view of one embodiment of cable adaptor 150. In this embodiment, a 0.185-inch diameter cylinder of medical-grade stainless steel (type 316L) is machined with a 0.120-inch through hole 151, threads 157 (for example, 8–60 threads) that correspond to threads in the female threaded opening 115 of housing 110, and shoulder 156, as shown.

Figure 1G:
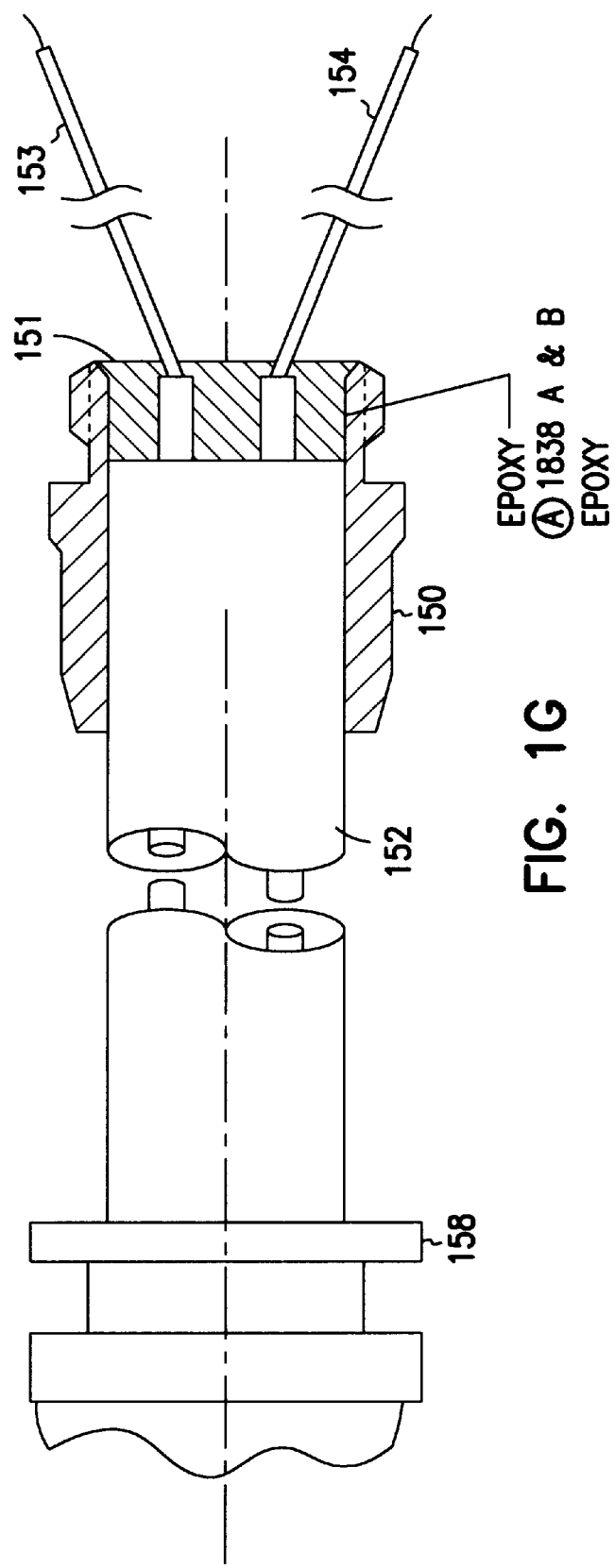
FIG. 1G shows a cross-section view of cable adaptor 150 assembled to cable 152.

FIG. 1G shows a cross-section view of one embodiment of cable adaptor 150 assembled to cable 152. In this embodiment, cable 152 is sealed to hole 151 of cable adaptor 150 using ScotchWeld 1838-type epoxy (parts A and B)(3M adhesives Division, 3M Center, Building 220-7E-01, St. Paul, Minn. 55144-1000). In this embodiment, cable 152 includes two wires 153 and 154, wherein the insulation is stripped so that it is slightly recessed within the inner end of hole 151, and two #36 AWG (American Wire Gauge) wires of length as required are soldered between the end of the cable 152 and the alumina substrate of amplifier 190, thus extending the ends of wires 153 and 154 with wire of a workable length so that they can be soldered to amplifier 190. In one embodiment, strain relief 158 is provided to support cable 152 at the sensor holding and positioning device apparatus 200 that holds arterial pulse pressure sensor 100.

Figure 1H:
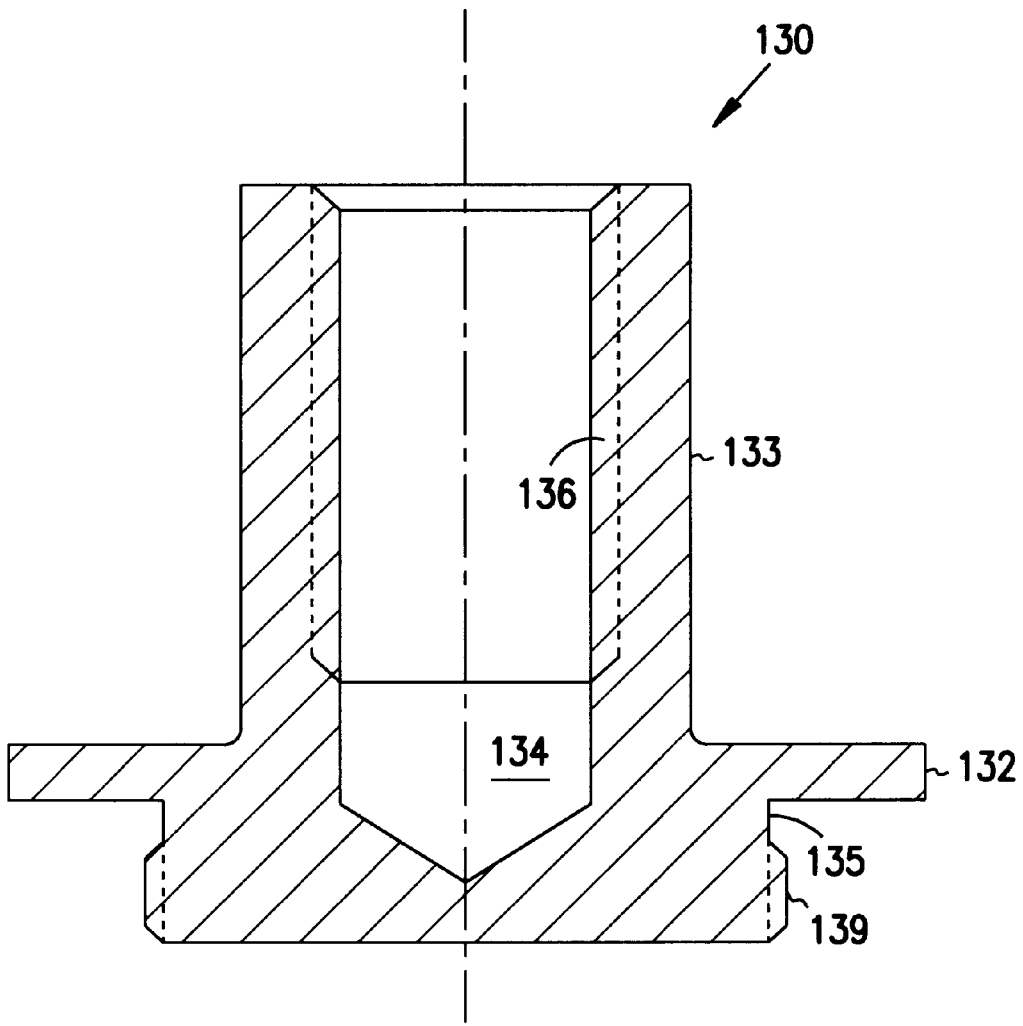
FIG. 1H shows a cross-section view of one embodiment of cover 130.

FIG. 1H shows a cross-section view of one embodiment of cover 130. In this embodiment, a 0.500-inch diameter cylinder (0.425 inches long) of type 316L stainless steel is machined with boss 133 having a 0.136-inch-diameter blind hole 134 that is 0.35 inches deep, and then is machined with female threads 136. Female threads provide a means for attaching arterial pulse pressure sensor 100 to sensor holding and positioning device 200 that can move or locate, and raise and/or lower arterial pulse pressure sensor 100 to a desired location and hold-down pressure on a subject's wrist overlying the radial artery, and that can maintain arterial pulse pressure sensor 100 at that desired location and hold-down pressure. The outer diameter of the upper 0.315 inches of cover 130 is machined to a cylindrical diameter of 0.238 inches as shown, leaving shoulder 132. The lower 0.080 inches of cover 130 is also machined to match the opening in the top of housing 110, and male threads 139 that correspond to female threads 119 in the top of housing 110 are formed. Recess 135 to accommodate O-ring gasket 140 is also formed, as shown.

Figure 1I:
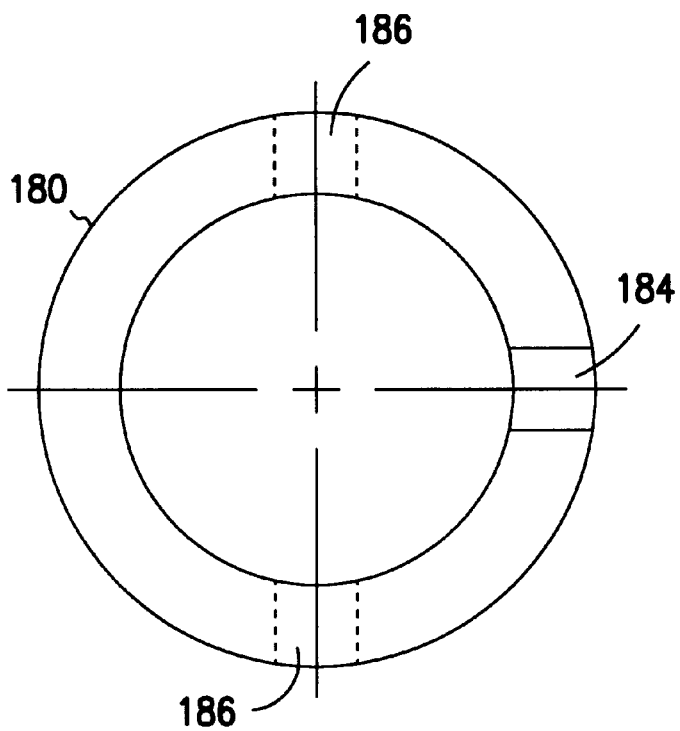
FIG. 1I shows a top view of one embodiment of DPCE-holder ring 180.
Figure 1J:
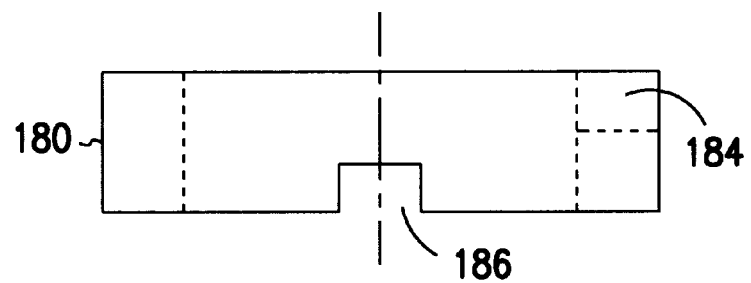
FIG. 1J shows a side view of one embodiment of DPCE-holder ring 180.

FIG. 1I shows a top view, and FIG. 1J shows a side view, of one embodiment of DPCE-holder ring 180. In this embodiment, DPCE-holder ring 180 is a cylindrical ring, 0.09 inches thick, and having a 0.325-inch outer diameter and a round 0.213-inch through hole. A slot 186 that is 0.064 inches wide and 0.030 inches deep is machined in the lower surface through both walls, and a slot 184 that its 0.051 inches wide and 0.030 inches deep is machined in the upper surface, but only through one wall, as shown. Slot 184 is used as a reference during machining and assembly operations.

Figure 1K:
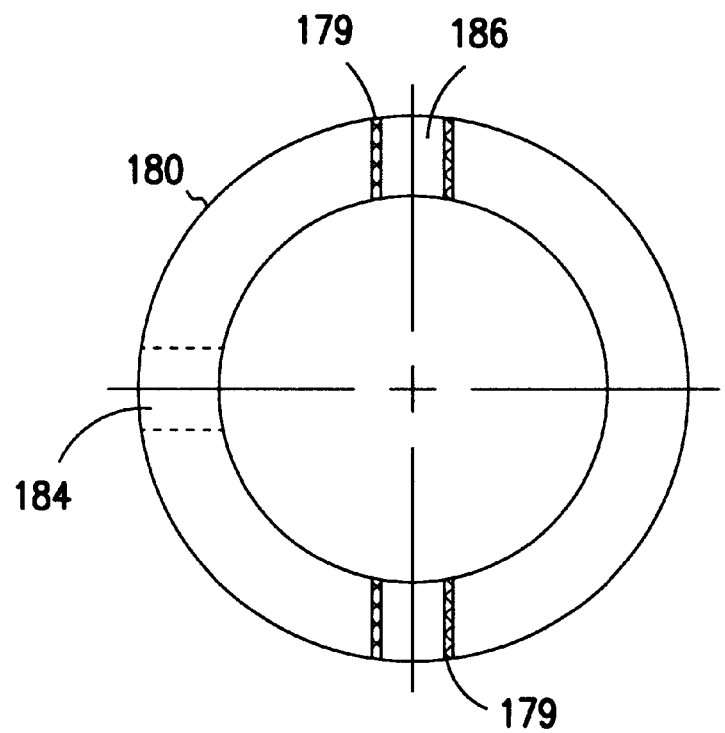
FIG. 1K shows a bottom view of one embodiment of DPCE-holder ring 180, after epoxy potting.
Figure 1L:
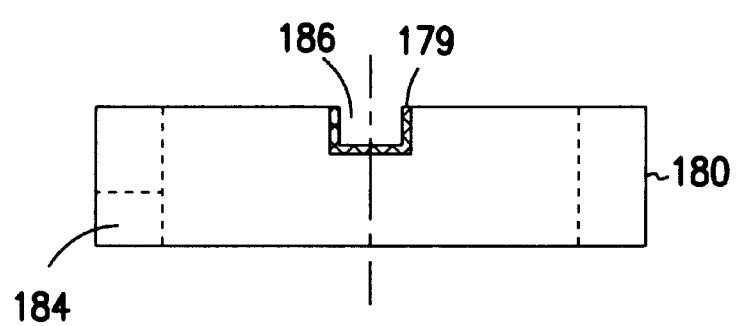
FIG. 1L shows a side view of one embodiment of DPCE-holder ring 180, after epoxy potting.

FIG. 1K shows a bottom view, and FIG. 1L shows a side view, of one embodiment of DPCE-holder ring 180, after epoxy potting. After machining as shown in FIGS. 1I and 1J, slot 186 is filled using epoxy type Stycast 2651 epoxy/catalyst 9 epoxy resin hardener (available from Emerson & Cuming Specialty Polymers, a division of National Starch & Chemical, 55 Hayden Avenue, Lexington, Mass. 02173; herein called "2651/Cat 9" by "E&C Company") and cured in an oven at 200° F. for a minimum of 30 minutes. The epoxy 179 in slot 186 is then remachined to 0.051 inches wide and 0.017 inches deep, so that DPCE 170 is electrically insulated from DPCE-holder ring 180, and yet protrudes so that electrical contact can be made between the 0.021-inch-thick DPCE 170 and housing shoulder 112.

Figure 1N:
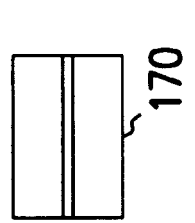
FIG. 1N shows an end view of one embodiment of DPCE 170.
Figure 1M:
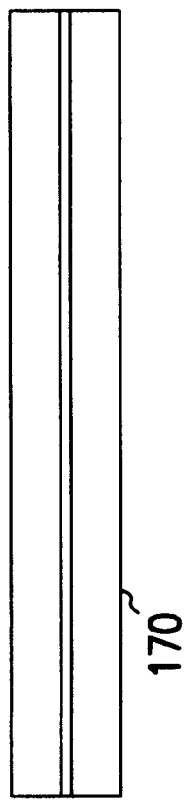
FIG. 1M shows a side view of one embodiment of DPCE 170.

FIG. 1M shows a side view, and FIG. 1N shows an end view, of one embodiment of DPCE 170. In the embodiment shown, a piezoelectric double-plate ceramic element (DPCE) that is 0.021 inches thick is cut to 0.180 inches long and 0.050 inches wide. The top surface forms one electrical contact (to which a wire is soldered, and the wire is then attached to amplifier 190), and the bottom surface forms the other electrical contact (which is made by contact to housing shoulder 112) once DPCE-holder ring 180 is secured using epoxy. In one embodiment, piezoelectric DPCE 170 is a ceramic piezoelectric block cut from a bulk plate or sheet of Bimorph® material (e.g., from a sheet of PZT-5A originally measuring 1.5 inches long by 0.75 inches wide by 0.021 inches thick) available from Morgan Matroc, Inc., Electro Ceramics Division, Bedford, Ohio. Bimorph® is a registered tradename of Morgan Matroc, Inc., Electro Ceramics Division, for a double-plate ceramic element. The two thin plates are bonded together so they amplify their piezoelectric actions. A DPCE generates greater voltage when bent, deformed or displaced than does a single-plate ceramic element.

Figures 1, 10:
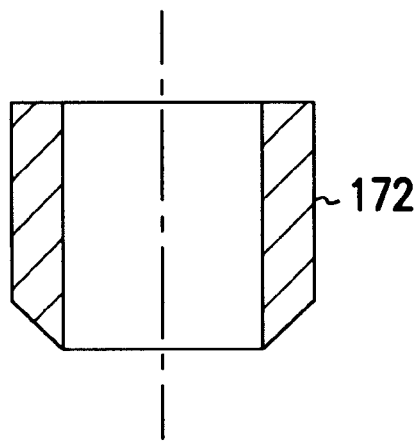
Figures 2, 10:
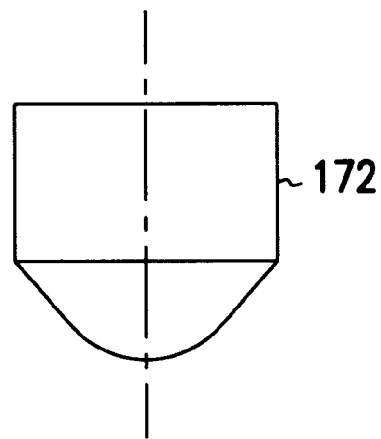

FIG. 1O-1 shows a side view of one embodiment of a DPCE post 172. In this FIG. 1O-1 embodiment, post 172 is aluminum alloy 6061-T6, and is 0.047 inches in diameter and 0.039 inches high with a 0.031-inch-diameter through hole (making a pipe-like structure), in order to provide a better surface configuration for epoxy to adhere to. In this embodiment, the lower end (which will be placed against diaphragm 120) of the outer edge of the post 172 is beveled at a 45-degree angle×0.008 inch. The flat upper face end of the post 172 and inner surface of the 0.031-inch-diameter through hole in post 172 are secured using epoxy to the bottom of DPCE 170 (using Epo-Tek 301 epoxy (available from Epoxy Technology, 14 Fortune Drive, Billerica, Mass. 01821)). FIG. 1O-2 shows a side view of another embodiment of DPCE post 172. In this FIG. 1O-2 embodiment, post 172 is aluminum alloy 6061-T6, and is 0.040 inches in diameter and 0.039 inches high. In this FIG. 1O-2 embodiment, the lower end is beveled at a 45° angle and the point (which will be placed against diaphragm 120) is machined to a spherical radius. The upper face is secured to the bottom of DPCE 170 using epoxy and hardener as described just above. In yet another embodiment, post 172 is replaced with a 1 millimeter steel ball, attached to DPCE 170 using epoxy adhesive or other attachment means. Post 172 with the 0.031-inch-diameter through hole is preferred over the ball embodiment because of the flat upper surface of the post and the interior surface of the through hole which make for a more secure assembly when secured with epoxy adhesive, and because a steel ball has a polished surface to which it is difficult to achieve a secure epoxy bond. For some embodiments using a ball, the side of the ball being secured using epoxy is textured, for example by chemical etching, in order to achieve a better bond.

Figure 1P:
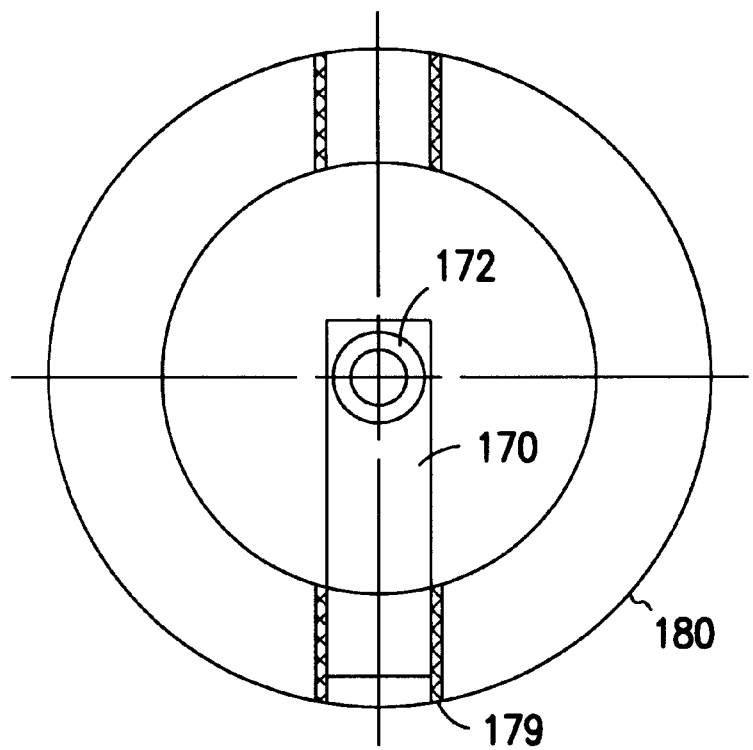
FIG. 1P shows a bottom view of one embodiment of DPCE-holder ring 180, after assembling DPCE 170 and post 172.
Figure 1Q:
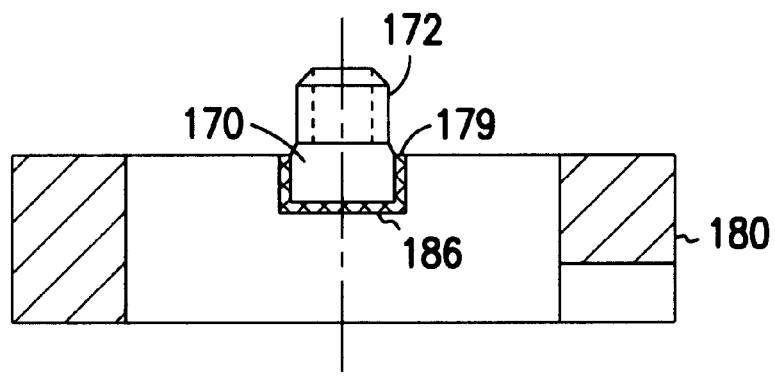
FIG. 1Q shows a side view of one embodiment of DPCE-holder ring 180, after assembling DPCE 170 and post 172.

FIG. 1P shows a bottom view, and FIG. 1Q shows a side view, of one embodiment of DPCE-holder ring 180, after assembling DPCE 170 and post 172. DPCE 170 is secured using epoxy into to the insulating epoxy 179 as remachined in potted slot 186 of DPCE-holder ring 180 as shown in FIGS. 1P and 1Q, using ScotchWeld 1838/A and B epoxy, and cured for 30 minutes at 150° F. In this, and all other embodiments, where DPCE 170 is part of an assembly which needs heat to cure epoxy, epoxy is cured at 150° F. to preclude any damage to the bonding agent used to bond the double plates of DPCE 170 since this bonding agent may fail at temperatures above 190° F. Post 172 is secured using epoxy to DPCE 170 as shown in FIGS. 1P and 1Q using Epo-Tek 301, and the epoxy is cured for 30 minutes at 150° F.

Figure 1R:
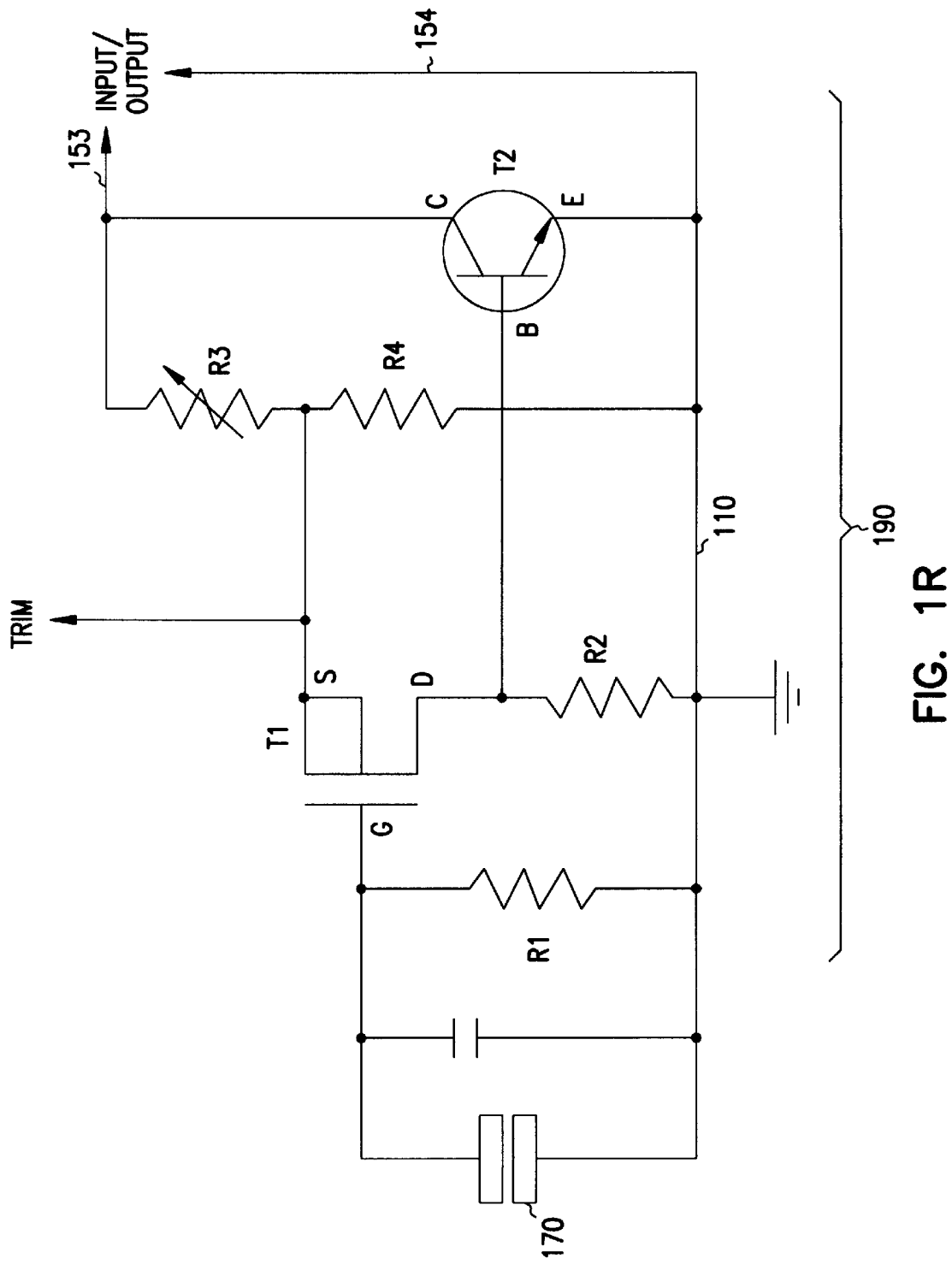
FIG. 1R shows a schematic circuit diagram of amplifier 190.

FIG. 1R shows a schematic circuit diagram of amplifier 190. In one embodiment, amplifier 190 is assembled on an alumina substrate 0.015 inches thick, 0.250 inches by 0.180 inches in area, and having solderable silver conductor material printed thereon. The circuit of amplifier 190 includes DPCE 170, $2 \times 10^{10}$–ohm resistor R1 (for example, part number CS1004M2008KS available from Ohmcraft, Inc., 3800 Monroe Avenue, Pittsford, N.Y. 14534), type ZVP3306F p-channel MOSFET transistor T1 (available from ZETEX Inc., 47 Mall Drive, Commack, N.Y. 11725), 1000-ohm resistor R2, 6200-ohm (trim by parallel resistor) resistor R3, 5600-ohm resistor R4 (in one embodiment, resistors R2, R3, and R4 are printed on the alumina substrate), and NPN transistor T2 (type MMBT3904 available from Diodes Incorporated, 3050 E. Hillcrest Dr., Westlake Village, Calif. 91362-3154). In one embodiment, resistor R3 is trimmable by soldering another suitable resistor in parallel to resistor R3 in order to lower the effective resistance of the combination to a desired value. In another embodiment, resistor R3 is made to some suitable starting resistance, and then laser trimmed to a final value by means well known to the art. In one embodiment, transistors T1 and T2 are surface-mount technology (SMT) parts. One surface of DPCE 170 is grounded to housing 110. The other surface of DPCE 170 is coupled to gate G of transistor T1, the source of T1 to the junction between voltage-divider resistors R3 and R4 which are connected across input/output wire 153 and ground. Resistor R2 is coupled between drain D of transistor T1, and ground. Drain D of transistor T1 is coupled to the base B of transistor T2; emitter E of transistor T2 is connected to ground (which is connected to ground wire 154); and collector C of transistor T2 is connected to input/output wire 153. Because the alumina substrate of amplifier 190 is insulating, it can be secured using epoxy adhesive directly to the top of DPCE-holder ring 180. In another embodiment, an amplifier platform is provided on the top of DPCE-holder ring 180.

The extremely high resistance of R1, along with the high input impedance of transistor T1 help to provide a frequency response for arterial pulse pressure sensor 100 that extends well below 1 hertz. In addition, by providing amplification within the shielded space enclosed by housing 110, diaphragm 120, and cover 130, and outputting a signal having a sensitivity of approximately of 1 volt per 100 mm of mercury pressure or 0.5 volts/psi (volts per pound per square inch of pressure), the effect of any environmental electromagnetic noise picked up by radiation into cable 152 is minimized.

In one embodiment, the sensitivity of arterial pulse pressure sensor 100 is trimmed to approximately (i.e., within a desired tolerance of) 1 volt per 100 mm of mercury pressure (mm Hg), for example, by adjusting the value of resistor R3 by wiring a suitable resistance in parallel with existing resistor R3. In one embodiment, a gate capacitor, wired in parallel to DPCE 170, is used to trim sensitivity and/or frequency response. In another embodiment, the sensitivity of arterial pulse pressure sensor 100 is trimmed to 0.5 volt per PSI (pound / square inch of pressure). (For reference, 1 PSI=about 51.8 mm Hg). In one embodiment, the low frequency limit is as low as 0.05 hertz (−3dB), and the upper frequency range is approximately 250 hertz, with a full-scale linearity of within 1% across an operating pressure range of 0 to 300 mm mercury (i.e., is about 0 to 6 PSI), and an operating temperature range of 0 to 50 degrees C.

Figure 1S:
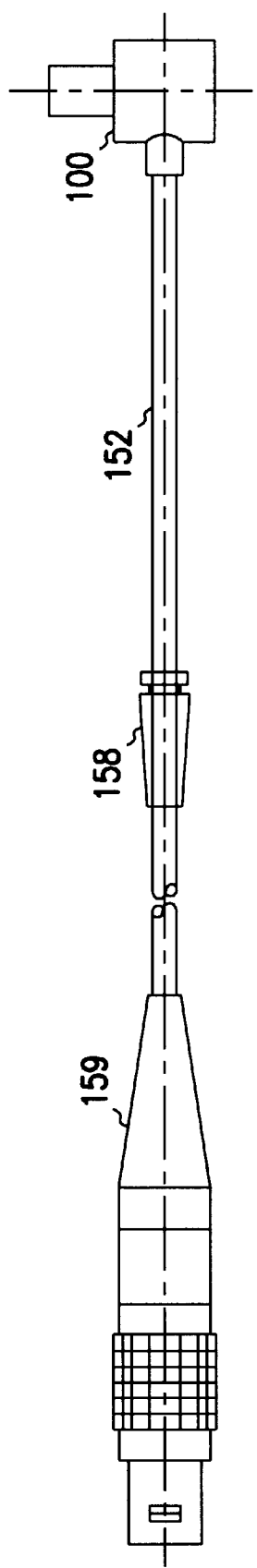
FIG. 1S shows an exterior side view of one embodiment of a complete arterial pulse pressure sensor 100 including cable 152, connector 159 and strain relief 158.

FIG. 1S shows a side view of one embodiment of a complete fabrication of arterial pulse pressure sensor 100 including cable 152, strain relief 158 and connector 159. In one embodiment, connector 159 is a LEMO-type connector, available from Lemo USA Inc./Redel, 335 Tesconi Cir., P.O. Box 11488, Santa Rosa, Calif. 95401.

Description

Arterial pulse pressure sensor 100 is a high-sensitivity, medical-grade, sealed piezoelectric microphone designed for detecting sound in humans and animals resulting from blood flow pulses. The sensing element (DPCE 170) is piezoelectric. The case material of arterial pulse pressure sensor 100 is medical-grade stainless steel (type 316L). It has internal microelectronics that condition the raw high-impedance output from the piezoelectric element DPCE 170 to provide a useful low-impedance voltage signal. The sensor has a flexible, integrally attached, output cable 152.

Installation and Use

Arterial pulse pressure sensor 100 may be used as a direct-contact microphone applied to the subject's skin or as an airborne sound/pressure sensor. The sensing surface is the circular area opposite the circular area of cover 130 with the 0.238 inch diameter boss. Although the overall diameter of the sensor is 0.500 inch, the sensing surface has a diameter of approximately 0.44 inch. When used as a direct-contact microphone, care should be taken not to push too hard against the skin. Maximum force should be no greater than 10 pounds and evenly distributed across the sensing surface. Avoid point loading on the sensing surface, especially in the center, since excessive force will likely cause the internal piezoelectric element (DPCE 170) to fail.

Powering

In one embodiment, arterial pulse pressure sensor 100 is powered with a constant-current power source, such as Model 5020 Power Conditioner available from Apollo Research Corporation (West Seneca, N.Y.) or any of the many constant-current power conditioners supplied by several other piezoelectric sensor manufacturers. The power-source voltage may be as low as about +10 volts and should be no higher than about +30 volts. Constant current supplied to the sensor may be any value between 2 and 8 milliamperes, however 2 milliamperes is recommended. Such a circuit can be provided by placing a 2 milliampere constant-current diode between a 12-volt supply voltage and the collector of transistor T2. A non-current limited voltage should never be applied to the sensor as this will likely destroy the internal electronics.

Assembly Procedure for One Embodiment of Arterial Pulse Pressure Sensor 100

1. Visually inspect all parts and remove any burrs. Clean with Lenium ™ (available from Petroferm Inc., 5415 First Coast Hwy., Fernandina Beach FL 32034) and denatured ethanol.
2. Mark the housing 110 with a label.
3. Spotweld diaphragm 120 to housing 110 using a diaphragm tack welding fixture to center the diaphragm 120 and a tack welding arbor to hold the housing 110. Spotwelder setting at 1.0% first pulse and 2.0% second pulse. Minimum 4 places, equally spaced.
4. Weld the diaphragm 120 to the housing 110 using a pulsed NdYAG laser welder; weld settings; pulse rate: 40/sec, pulse width: 1, joules/pulse: 0.3, and seconds/rev: 5.5. Use a diaphragm welding pilot to hold the housing and also use a diaphragm welding heat sink.
5. Pot and cure DPCE-holder ring 180 using Stycast 2651/catalyst 9 (E & C Company). Cure in oven at 200° F. for minimum of 30 minutes. Re-machine slot to 0.051 inches wide and 0.017 inches deep.
6. Assemble the 0.021 inch-thick DPCE 170 to the re-machined insulated slot in DPCE-holder ring 180 as shown in FIGS. 1P and 1Q, using ScotchWeld 1838/A and B epoxy (3M Adhesives Division, 3M Center, Building 220-7E-01, St. Paul, MN 55144-1000). Cure epoxy 30 minutes at 150° F.
7. Assemble post 172 to DPCE 170 as shown in FIGS. 1P and 1Q using Epo-Tek 301 (available from Epoxy Technology, 14 Fortune Drive, Billerica, MA 01821). Cure epoxy 30 minutes minimum at 150° F.
8. Cut cable 152 to the required length and assemble into cable adapter 150 using Epo-Tek 301 parts A and B epoxy. Cure in oven at 150° F. for a minimum of 30 minutes. Refer to FIG. 1H. Solder a #36 AWG about 1 inch long to each conductor. Pot wires with ScotchWeld 1838/A & B epoxy. Cure 30 minutes minimum at 150° F.
9. Apply ScotchWeld 1838/A and B epoxy to the chamfered end of post 172. Apply ScotchWeld 1838/A and B epoxy to the side of the housing 110 as shown in Main Assembly FIG. 1A. Push the DPCE-holder ring assembly (parts 180, 179, 170, and 172) into the housing 110 until it firmly seats on the flat surface 112 of the housing 110. Use a fixture to hold the assembly (parts 180,179, 170, and 172) in place while curing the epoxy. Cure in oven at 150° F. for minimum 1.0 hour. Solder a #44 AWG base wire to the DPCE 170 as shown in Main Assembly FIG. 1A.

-continued

Assembly Procedure for One Embodiment of Arterial Pulse Pressure Sensor 100

10. Apply a small amount of Epo-Tek H20E A and B conductive epoxy (available from Epoxy Technology, 14 Fortune Drive, Billerica, MA 01821) to the joint between the DPCE-holder and the Housing. Cure 30 minutes minimum at 150° F.
11. Assemble the Amplifier.
12. Assemble Amplifier Assembly to the housing as shown in FIG. 1A using ScotchWeld 1838/A and B epoxy. Cure at 150° F. for 30 minutes.
13. Assemble the Cable Subassembly (FIG. 1G) into the Housing 110 as shown in Assembly (FIG. 1A) using ScotchWeld 1838/A and B epoxy. Solder cable conductors to amplifier. Cure epoxy at 150° F. for 30 minutes.
14. Pott the cable and cable adaptor to the housing as shown in FIG. 1A using ScotchWeld 1838/A and B. Cure 30 minutes at 150° F.
15. At this point, initial calibration is done as follows. Install sensor 100 into a calibration fixture. Perform an initial test. If the sensitivity of sensor 100 is within tolerance, then proceed to step 16. Otherwise, if the sensitivity of sensor 100 is too high, trim the sensitivity by selecting an appropriate gate capacitor and/or R3 trim resistor to bring the sensitivity within tolerance. (If the sensitivity of sensor 100 is too low, something is wrong with it, and generally the sensor must be repaired or scrapped.)
16. Place the O-Ring 140 on the Cover 130 and assemble to the housing 110 as shown in Main Assembly FIG. 1A using ScotchWeld 1838-type epoxy (parts A and B)(3M Adhesives Division, 3M Center, Building 220-7E-01, St. Paul, MN 55144-1000). Cure epoxy at 150° F. for 30 minutes.
17. The sensor is now ready for final calibration. This calibration includes final determination of sensitivity and frequency response.

In operation, arterial pulse pressure sensor 100, in one embodiment, is used to measure the arterial pulse pressure waveform of the radial artery at the wrist of a human. In one embodiment, the pulse is palpated and the location of the radial artery marked with a pen. The arterial pulse pressure sensor 100 is then manually held in place, or preferably, a mechanical sensor holding and positioning device is used to maintain the sensor in place on the skin overlying the subject's radial artery, and to maintain an optimal hold-down pressure of the sensor in order to obtain a desired blood pressure waveform for a desired length of time.

Figure 2A:
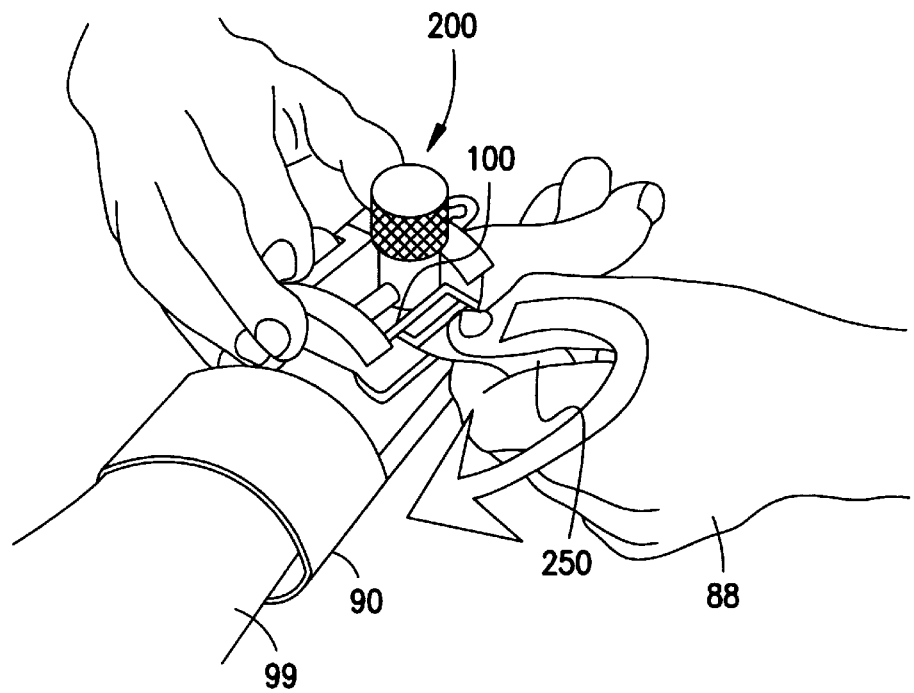
FIG. 2A is an isometric view showing one embodiment of arterial pulse pressure sensor 100 as assembled to a sensor holding and positioning device 200 and being applied to a radial artery of a patient 99.

In one embodiment, the position of the subject's wrist is maintained in a fingers open, stable and relaxed position by a suitable wrist stabilizer 90, such as shown in FIG. 2A, in order to optimally position and stabilize the portion of the radial artery from which the measurement is being obtained.

Figure 2B:
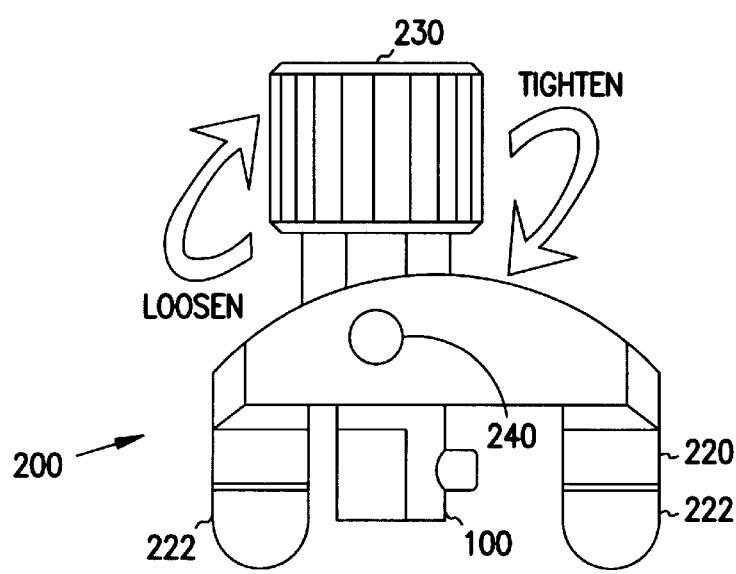
FIG. 2B is a end view showing one embodiment of arterial pulse pressure sensor 100 as assembled to a sensor holding and positioning device 200.
Figure 2C:
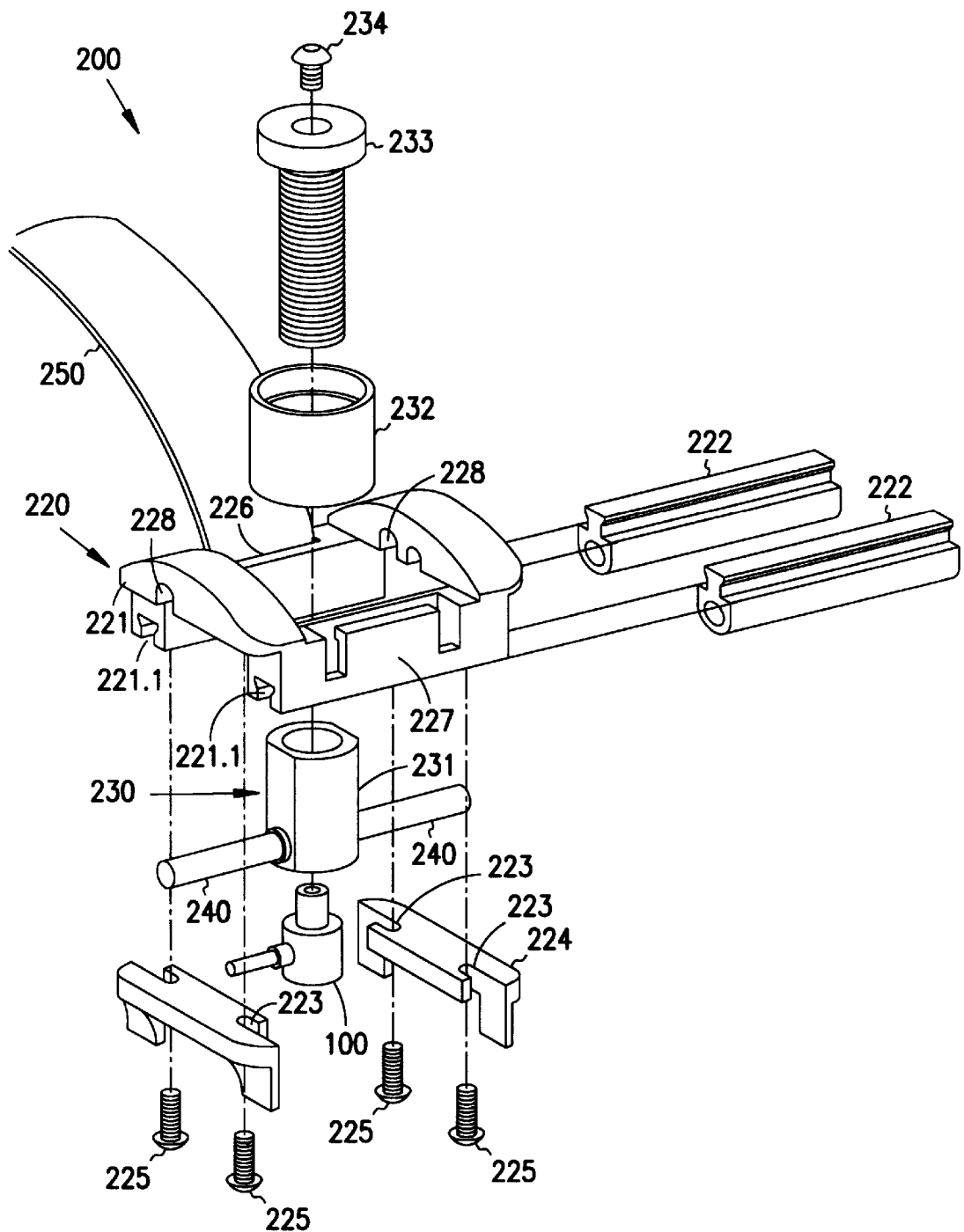
FIG. 2C is an exploded isometric view showing one embodiment of arterial pulse pressure sensor 100 as assembled to a sensor holding and positioning device 200.

FIG. 2A shows a view of a wrist stabilizer 90, a sensor holding and positioning device 200, and sensor 100 according to the present invention being applied to a radial artery of a subject 99. Healthcare professional 88 wraps strap 250 around the outside of wrist stabilizer 90, thus leaving some portion of the circumference of the subject's wrist open to allow return of venous blood. In a preferred embodiment, strap 250 is permanently attached to base 220 on the side closest to axle 240, and removably buckled to the other side (the side having the largest opening). In another embodiment, as shown in FIG. 2A, the buckle is attached to the side closest to axle 240, and the other end of strap 250 is attached to the side having the largest opening next to sensor 100. FIG. 2B is an end view showing one embodiment of arterial pulse pressure sensor 100 as assembled to a sensor holding and positioning device 200 having two soft rubber feet 222. Adjustment knob 230 adjusts the height, and thus the hold-down pressure, of sensor 100 against the skin of the subject. FIG. 2C is an exploded isometric view showing one embodiment of arterial pulse pressure sensor 100 as assembled to a sensor holding and positioning device. (Some embodiments of wrist stabilizer 90 and sensor holding and positioning device 200 are described in co-pending application entitled "APPARATUS AND METHOD FOR HOLDING AND POSITIONING AN ARTERIAL PULSE PRESSURE SENSOR" filed on even date herewith and incorporated herein by reference.).

Figure 3A:
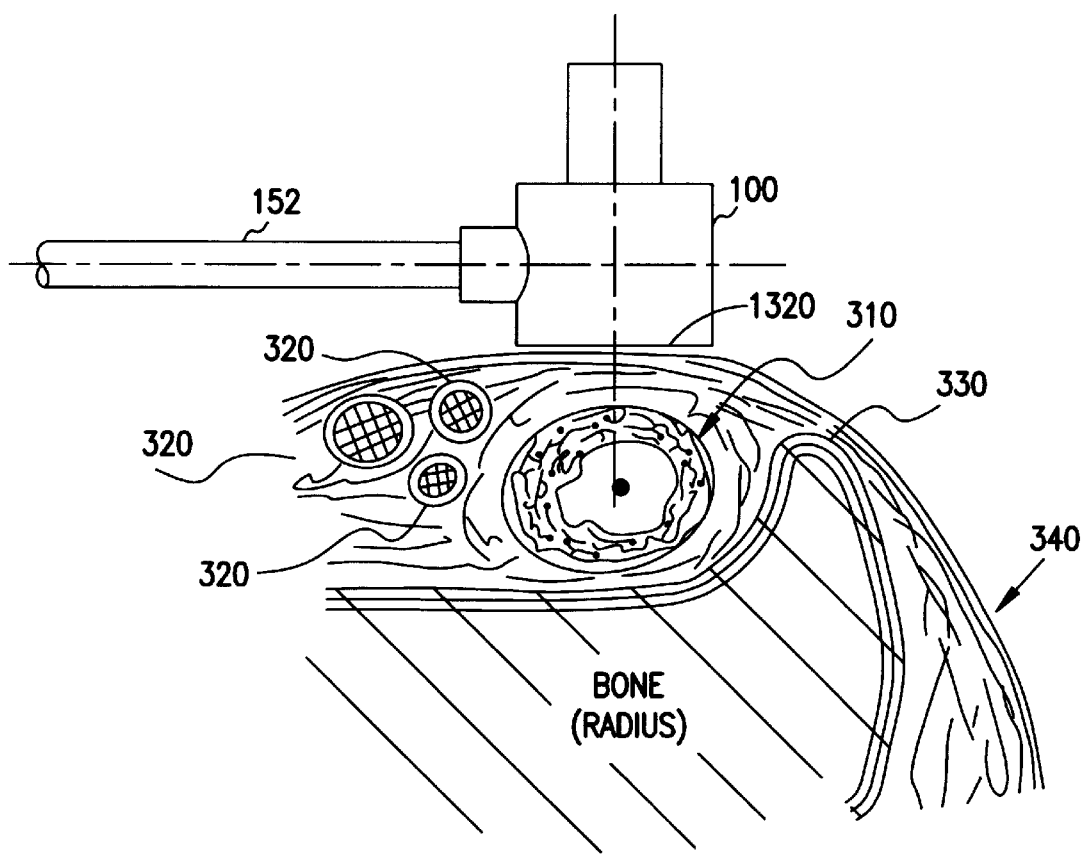
FIG. 3A is a cross-section view of a human wrist showing placement of a small diameter arterial pulse pressure sensor 100 over the radial artery.
Figure 3B:
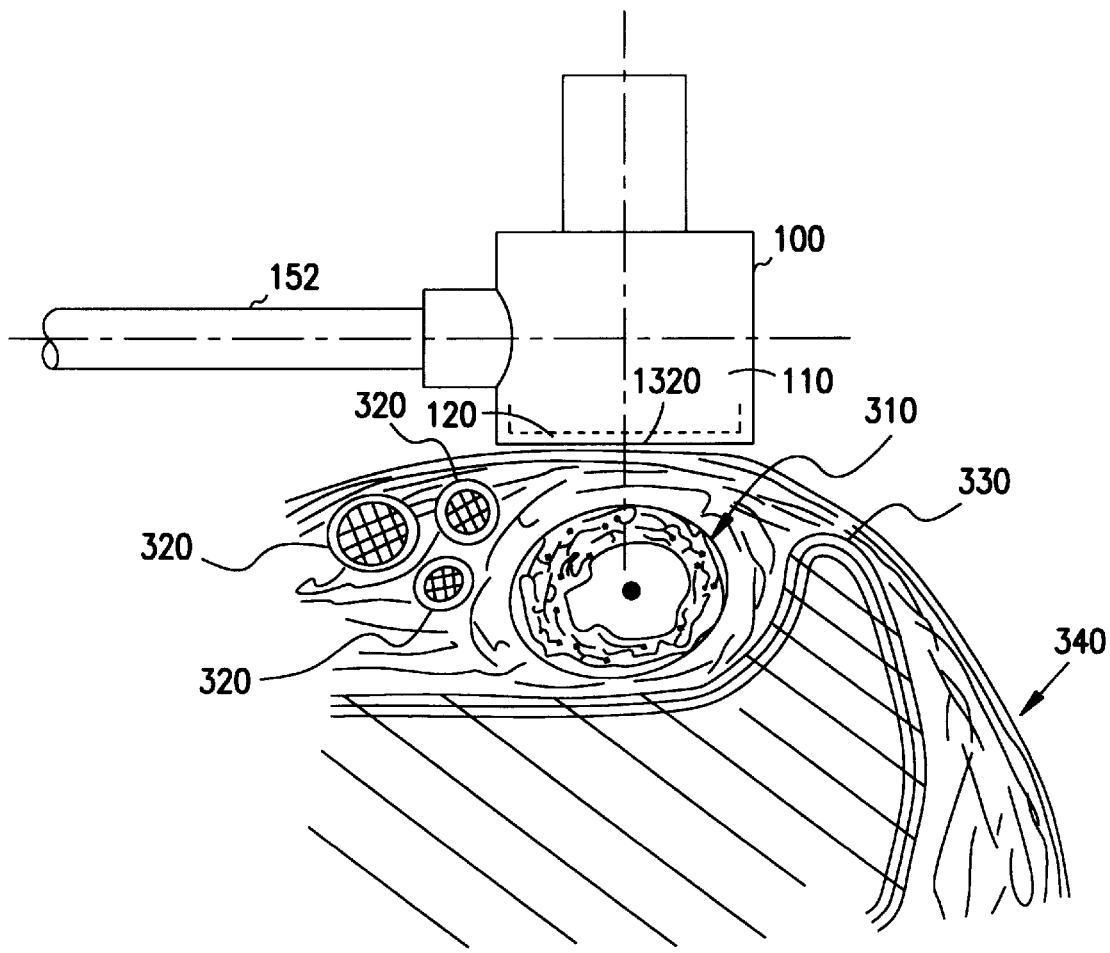
FIG. 3B is a cross-section view of a human wrist showing placement of a medium diameter arterial pulse pressure sensor 100 over the radial artery.
Figure 3C:
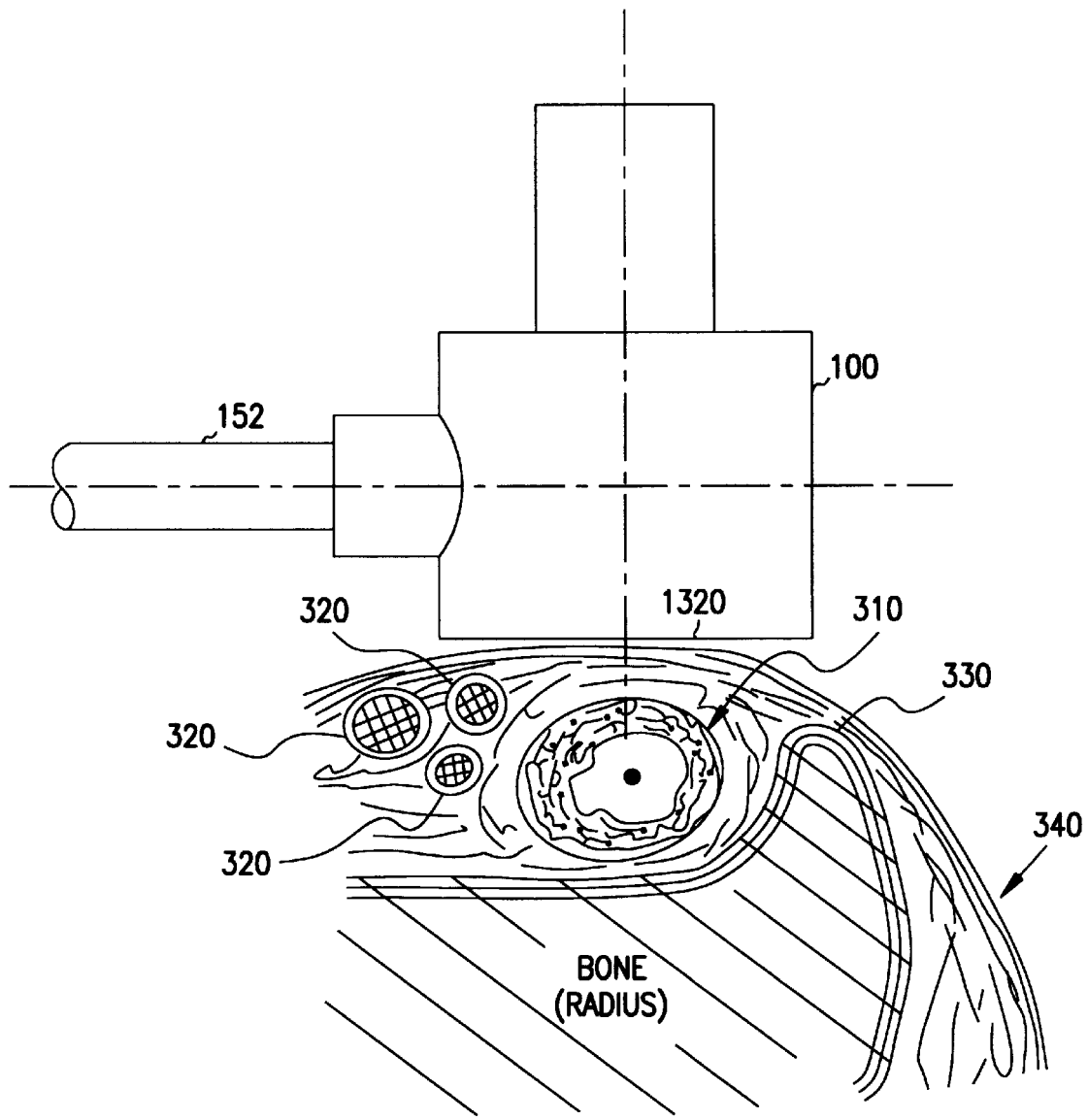
FIG. 3C is a cross-section view of a human wrist showing placement of a large diameter arterial pulse pressure sensor 100 over the radial artery.

FIG. 3A is a cross-section view of a human wrist showing placement of a small diameter arterial pulse pressure sensor 100 over the radial artery 310. Hold-down pressure has not yet been applied to sensor 100. While a sensor having a relatively small diaphragm such as shown in FIG. 3A can obtain a blood-pressure-waveform signal when placed directly over the radial artery 310, such placement is more difficult to obtain, and signal strength is reduced as compared to a sensor having a diameter of approximately 0.5 inches. FIG. 3B is a cross-section view of a human wrist showing placement of a medium diameter arterial pulse pressure sensor 100 over the radial artery 310. FIG. 3C is a cross-section view of a human wrist showing placement of a large-diameter arterial pulse pressure sensor 100 over the radial artery 310.

FIG. 3B is a cross-section view of a wrist showing placement of arterial pulse pressure sensor 100 over the radial artery 310 before hold-down pressure is applied to sensor 100. Radial artery 310 lies between tendons 320 and the ridge of the radius bone 330, under skin 340. The large dot in the center of the arterial lumen of artery 310 represents the longitudinal axis of the radial artery 310. The flat surface 1320 of diaphragm 120 is parallel to the axis of artery 310. It has been discovered that a diaphragm diameter of approximately 0.5 inches is large enough to provide a good waveform signal (even if not exactly centered over the artery 310), yet small enough that housing 110 does not form a bridge (i.e., as shown in FIG. 3C) between tendons 320 and the ridge of the radius bone 330 that prevents comfortable application of adequate hold-down pressure on artery 310 in order to get the desired blood pressure waveform from the radial artery 310. A diameter between approximately 0.3 inches and approximately 0.7 inches will work. In particular, a diameter between approximately 0.4 inches and approximately 0.6 inches is preferred.

Terminology

As used herein, a "wrist stabilizer" stabilizes or immobilizes the wrist (and also the radial artery 310) during measurement, and positions the wrist so the radial artery 310 is as close as possible to the skin surface, in order to obtain an optimal signal. A "bridge apparatus" or "sensor holding and positioning device" includes everything that holds the sensor suspension over an artery. The bridge apparatus can be made of one or more pieces. In one preferred embodiment, the bridge apparatus is structured and used so that it is supported by the subject's body on either or both sides of the artery without the bridge apparatus itself putting any pressure on the artery being measured. A "sensor suspension" is mounted to the bridge apparatus and allows movement of the sensor holding and positioning device in X and/or Y directions (roughly parallel to the plane of the skin above the radial artery to be measured) in order that the sensor holding and positioning device can be moved and held over the artery. The sensor suspension can be made of one or more pieces. A "sensor holder" is held by the suspension and includes a member movable in the Z direction (substantially perpendicular to the plane of the skin above the artery to be measured), in order to move sensor 100 up and down. This allows the user to apply the proper amount of hold-down pressure on arterial pulse pressure sensor 100 in order to obtain the best blood-pressure waveform.

In one embodiment, the waveform obtained from arterial pulse pressure sensor 100 is analyzed to determine vascular compliance or impedance according to the teaching of U.S. Pat. No. 5,316,004, issued May 31, 1994, and incorporated herein by reference.

In other embodiments, arterial pulse pressure sensor 100 is used to measure other sounds or pressure waveforms on the human body (or animal bodies), such as fetal heartbeats or patient heartbeats, breathing sounds, swallowing or digestive sounds, tendon or joint noises, or other body sounds or pressure waveforms. Because of its excellent frequency response, particularly at extremely low frequencies, arterial pulse pressure sensor 100 can be used to obtain pressure or sound waveforms that are not accurately measurable using other sensors such as an audio microphone that is typically sensitive to a range of 100 to 5,000 hertz, or even one sensitive to the human auditory range of about 20 to 20,000 hertz. In fact, most of the frequencies at the radial artery are typically below 10 hertz, precluding detection by the human ear.

The inventors believe that the present invention presents an acoustic method for measuring blood-pressure waveforms that are different than the four methods for measuring blood pressure described herein above in the Background. The acoustic method of the present invention measures sound waves or pressure changes from as low as below 0.1 hertz to as high as 250 hertz or even as high as 5,000 hertz. By including such a wide range of frequencies, more clinical information can be derived as to the condition of the subject's vascular system, and particularly, information as to vascular or arterial compliance or impedance may be more accurately measured non-invasively. This provides the ability to easily, quickly and accurately determine cardiovascular parameters from a subject, and thus afford the opportunity for preventive health measures, as well as to facilitate the treatment and monitoring of subjects with cardiovascular disease.

Further, the versatility and accuracy of the arterial pulse pressure sensor 100 of the present invention provides the opportunity to measure other sounds and pressure parameters of the human (and animal) body well beyond those described explicitly here.

In one embodiment, arterial pulse pressure sensor 100 is tested and calibrated by coupling arterial pulse pressure sensor 100 in parallel (hydraulically) with a standard sensor of suitable pre-determined sensitivity and accuracy, both sensors being displaced mechanically by a hydraulic line driven by a blood-pressure-systems calibrator such as BIO-TEK Model 601A Blood Pressure Systems Calibrator (available from Bio-Tek Instruments, Highland Park, Winooski, Vt. 05404-0998). The electrical signal from each sensor is connected to a power conditioner that provides the proper drive signal to the respective sensor (e.g., for the arterial pulse pressure sensor 100, a constant-current source of 2 milliamps, and for the standard sensor, a power supply wherein its output is standardized at one volt per 100 millimeters mercury), and that couples the output signal to a suitable detector, such as a dual-trace oscilloscope, that allows comparisons and/or calibration of the arterial pulse pressure sensor 100 under test.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A body-sound sensor comprising:

a housing (110);

a skin-contact diaphragm (120) attached across a recess or opening in the housing, a piezoelectric device (170) having a first portion mounted in a fixed relationship to the housing and a second portion displacementally coupled to the diaphragm; and a solid-state amplifier (190) having a signal input coupled to the device, wherein the device and amplifier together have a frequency response at least including a range from below approximately 1 hertz to above approximately 250 hertz.

2. The sensor according to claim 1, wherein the housing and the skin-contact diaphragm are stainless steel.

3. The sensor according to claim 2, wherein the diaphragm has a skin-contact surface with a skin-contact dimension of between approximately 0.4 inch and 0.6 inch, and wherein the sensor is used to acquire a signal from the radial artery.

4. The sensor according to claim 1, wherein the diaphragm has a skin-contact surface with a skin-contact dimension of between approximately 0.4 inch and 0.6 inch and wherein the sensor is used to acquire a signal from the radial artery.

5. A body-sound sensor comprising:

a housing (110)

a skin-contact diaphragm (120) attached across a recess or opening in the housing, a piezoelectric device (170) having a first portion mounted in a fixed relationship to the housing and a second portion displacementally coupled to the diaphragm; and a solid-state amplifier (190) having a signal input coupled to the device, wherein the device and amplifier together have a frequency response at least including a range from below approximately 1 hertz to above approximately 250 hertz, wherein the solid-state amplifier (190) includes a MOSFET input stage having an input resistance high enough to provide a frequency response that extends below approximately 0.1 hertz.

6. A body-sound sensor comprising:

a housing (110);

a skin-contact diaphragm (120) attached across a recess or opening in the housing, a piezoelectric device (170) having a first portion mounted in a fixed relationship to the housing and a second portion displacementally coupled to the diaphragm; and a solid-state amplifier (190) having a signal input coupled to the device, wherein the device and amplifier together have a frequency response at least including a range from below approximately 1 hertz to above approximately 250 hertz, wherein the solid-state amplifier (190) comprises:

an input/output signal wire;

a ground signal path;

a voltage divider, the voltage divider coupled between the input/output signal wire and the ground;

a drain resistor coupled to the ground;

a gate resistor coupled to the ground;

a MOSFET input transistor having a gate coupled to receive a signal from the piezoelectric device (170), a source coupled to an intermediate point of the voltage divider, and a drain, wherein the drain resistor is coupled between the drain and the ground, and the gate resistor is coupled between the gate and the ground; and a bipolar output transistor having a collector coupled to the input/output signal wire, an emitter coupled to the ground, and a base coupled to the drain of the input transistor.

7. The sensor according to claim 6, wherein the piezoelectric device (170) includes a piezoelectric double-plate ceramic element, wherein two thin plates are bonded together so they amplify their piezoelectric actions.

8. A body-sound sensor comprising:

a housing (110);

a skin-contact diaphragm (120) attached across a recess or opening in the housing, a piezoelectric device (170) having a first portion mounted in a fixed relationship to the housing and a second portion displacementally coupled to the diaphragm; and a solid-state amplifier (190) having a signal input coupled to the device, wherein the device and amplifier together have a frequency response at least including a range from below approximately 1 hertz to above approximately 250 hertz, wherein the piezoelectric device (170) includes a piezoelectric double-plate ceramic element, wherein two thin plates are bonded together so they amplify their piezoelectric actions.

9. The sensor according to claim 1, further comprising a constant-current source coupled to the amplifier.

10. The sensor according to claim 6, further comprising a constant-current source coupled to input/output wire of the amplifier.

11. A piezoelectric acoustical pressure sensor including:

a stainless-steel housing, the housing having a skin-contact diaphragm, the diaphragm having a skin-contact surface with a skin-contact dimension of between approximately 0.3 inch and 0.7 inch;

a piezoelectric device displacementally coupled to the diaphragm;

a solid-state amplifier within the housing having a signal input coupled to the device, the device and amplifier together having a frequency response of approximately 0.1 hertz to at least approximately 250 hertz and wherein the sensor is used to acquire a signal from the radial artery.

12. A piezoelectric acoustical pressure sensor including:

a stainless-steel housing, the housing having a skin-contact diaphragm, the diaphragm having a skin-contact surface with a skin-contact dimension of between approximately 0.3 inch and 0.7 inch;

a piezoelectric device displacementally coupled to the diaphragm;

a solid-state amplifier having a signal input coupled to the device, the device and amplifier together having a frequency response of approximately 0.1 hertz to at least approximately 250 hertz, wherein the solid-state amplifier (190) comprises:

an input/output signal wire;

a ground signal path;

a voltage divider, the voltage divider coupled between the input/output signal wire and the ground;

a drain resistor coupled to the ground;

a gate resistor coupled to the ground;

a MOSFET input transistor having a gate coupled to receive a signal from the piezoelectric device (170), a source coupled to an intermediate point of the voltage divider, and a drain, wherein the drain resistor is coupled between the drain and the ground, and the gate resistor is coupled between the gate and the ground; and a bipolar output transistor having a collector coupled to the input/output signal wire, an emitter coupled to the ground, and a base coupled to the drain of the input transistor.

13. A method for sensing body sounds comprising the steps of:

displacing a skin-contact diaphragm using changing pressure at a skin surface to create a diaphragm displacement;

converting the diaphragm displacement into a piezoelectric displacement;

generating an electrical signal representative of the piezoelectric displacement; and amplifying the electrical signal, wherein the steps of displacing, converting, and amplifying together have a frequency response at least including a range from below approximately 1 hertz to above approximately 250 hertz.

14. The method according to claim 13, wherein the diaphragm is stainless steel.

15. The method according to claim 14, wherein the diaphragm has a skin-contact surface with a skin-contact dimension of between approximately 0.4 inch and 0.6 inch, and is approximately 0.006 inch thick and wherein the method is used to acquire a signal from the radial artery.

16. The method according to claim 13, wherein the diaphragm has a skin-contact surface with a skin-contact dimension of between approximately 0.4 inch and 0.6 inch and wherein the method is used to acquire a signal from the radial artery.

17. A method for sensing body sounds comprising the steps of:

displacing a skin-contact diaphragm using changing pressure at a skin surface to create a diaphragm displacement;

converting the diaphragm displacement into a piezoelectric displacement;

generating an electrical signal representative of the piezoelectric displacement; and amplifying the electrical signal, wherein the steps of displacing, converting, and amplifying together have a frequency response at least including a range from below approximately 1 hertz to above approximately 250 hertz, wherein the step of amplifying includes using a MOSFET input stage having an input resistance high enough to provide a frequency response that extends below approximately 0.1 hertz.

18. A method for sensing body sounds comprising the steps of:

displacing a skin-contact diaphragm using changing pressure at a skin surface to create a diaphragm displacement;

converting the diaphragm displacement into a piezoelectric displacement;

generating an electrical signal representative of the piezoelectric displacement; and amplifying the electrical signal, wherein the steps of displacing, converting, and amplifying together have a frequency response at least including a range from below approximately 1 hertz to above approximately 250 hertz, wherein the step of amplifying comprises the steps of:

providing a constant-current source and a ground signal path;

coupling a voltage divider between the constant-current source and the ground;

coupling the signal from the piezoelectric displacement to a gate of a MOSFET input transistor, the MOSFET transistor having a source coupled to an intermediate point of the voltage divider, and a drain, wherein a drain resistor is coupled between the drain and the ground, and a gate resistor is coupled between the gate and the ground; and coupling a signal from the MOSFET transistor to a base of a bipolar output transistor having a collector coupled to the constant-current source, and an emitter coupled to the ground.

19. A method for sensing body sounds comprising the steps of:

displacing a skin-contact diaphragm using changing pressure at a skin surface to create a diaphragm displacement;

converting the diaphragm displacement into a piezoelectric displacement;

generating an electrical signal representative of the piezoelectric displacement; and amplifying the electrical signal, wherein the steps of displacing, converting, and amplifying together have a frequency response at least including a range from below approximately 1 hertz to above approximately 250 hertz, wherein the piezoelectric displacement is to a piezoelectric double-plate ceramic element, wherein two thin plates are bonded together so they amplify their piezoelectric actions.

20. A method for sensing body sounds comprising the steps of:

displacing a skin-contact diaphragm using changing pressure at a skin surface to create a diaphragm displacement;

converting the diaphragm displacement into a piezoelectric displacement;

generating an electrical signal representative of the piezoelectric displacement; and amplifying the electrical signal, wherein the steps of displacing, converting, and amplifying together have a frequency response at least including a range from below approximately 1 hertz to above approximately 250 hertz wherein the diaphragm has a skin-contact surface with a skin-contact dimension of between approximately 0.4 inch and 0.6 inch, and is approximately 0.006 inch thick, wherein the piezoelectric displacement is to a piezoelectric double-plate ceramic element, wherein two thin plates are bonded together so they amplify their piezoelectric actions.

* * * * *